(12) United States Patent
Inoue et al.

(10) Patent No.: US 9,273,079 B2
(45) Date of Patent: Mar. 1, 2016

(54) ORGANOMETALLIC COMPLEX, LIGHT-EMITTING ELEMENT, LIGHT-EMITTING DEVICE, ELECTRONIC DEVICE, AND LIGHTING DEVICE

(75) Inventors: Hideko Inoue, Kanagawa (JP); Yui Yamada, Kanagawa (JP); Nobuharu Ohsawa, Tochigi (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 815 days.

(21) Appl. No.: 13/534,497

(22) Filed: Jun. 27, 2012

(65) Prior Publication Data

US 2013/0002131 A1    Jan. 3, 2013

(30) Foreign Application Priority Data

Jun. 29, 2011    (JP) ................. 2011-144337

(51) Int. Cl.
| | |
|---|---|
| H01L 51/54 | (2006.01) |
| C09K 11/06 | (2006.01) |
| C07F 15/00 | (2006.01) |
| H05B 33/14 | (2006.01) |
| H01L 51/50 | (2006.01) |
| H01L 51/52 | (2006.01) |
| H01L 27/32 | (2006.01) |
| H01L 51/00 | (2006.01) |

(52) U.S. Cl.
CPC ............ *C07F 15/0033* (2013.01); *C09K 11/06* (2013.01); *H01L 51/0085* (2013.01); *H05B 33/14* (2013.01); *C09K 2211/1059* (2013.01); *C09K 2211/185* (2013.01); *H01L 27/3206* (2013.01); *H01L 51/0072* (2013.01); *H01L 51/0074* (2013.01); *H01L 51/504* (2013.01); *H01L 51/5016* (2013.01); *H01L 51/5028* (2013.01); *H01L 51/5265* (2013.01); *H01L 51/5278* (2013.01)

(58) Field of Classification Search
None
See application file for complete search history.

(56) References Cited

U.S. PATENT DOCUMENTS

| | | | |
|---|---|---|---|
| 6,908,695 B2 | 6/2005 | Seo et al. | |
| 7,045,955 B2 | 5/2006 | Seo et al. | |
| 7,148,076 B2 | 12/2006 | Seo et al. | |
| 7,332,857 B2 | 2/2008 | Seo et al. | |
| 7,413,916 B2 | 8/2008 | Seo et al. | |
| 7,550,173 B2 | 6/2009 | Seo et al. | |
| 7,572,522 B2 | 8/2009 | Seo et al. | |
| 7,579,089 B2 | 8/2009 | Seo et al. | |
| 7,629,025 B2 | 12/2009 | Yamazaki et al. | |
| 7,732,811 B2 | 6/2010 | Shitagaki et al. | |
| 7,737,630 B2 | 6/2010 | Seo et al. | |
| 8,101,771 B2 | 1/2012 | Nomura et al. | |
| 8,178,217 B2 | 5/2012 | Nomura et al. | |
| 8,293,921 B2 | 10/2012 | Nomura et al. | |
| 8,310,147 B2 | 11/2012 | Seo et al. | |
| 8,319,210 B2 | 11/2012 | Shitagaki et al. | |
| 8,354,786 B2 | 1/2013 | Yamazaki et al. | |
| 2002/0093283 A1 | 7/2002 | Seo et al. | |
| 2002/0139303 A1 | 10/2002 | Yamazaki et al. | |
| 2003/0010288 A1 | 1/2003 | Yamazaki et al. | |
| 2006/0036097 A1 | 2/2006 | Qiu et al. | |
| 2007/0085073 A1 | 4/2007 | Inoue et al. | |
| 2007/0222376 A1 | 9/2007 | Ohsawa et al. | |
| 2009/0072725 A1 | 3/2009 | Suzuki et al. | |
| 2009/0160324 A1 | 6/2009 | Nomura et al. | |
| 2011/0101854 A1 | 5/2011 | Inoue et al. | |
| 2011/0198988 A1 | 8/2011 | Inoue et al. | |
| 2011/0220882 A1 | 9/2011 | Inoue et al. | |
| 2012/0199818 A1 | 8/2012 | Nomura et al. | |
| 2013/0075713 A1 | 3/2013 | Shitagaki et al. | |

FOREIGN PATENT DOCUMENTS

| | | |
|---|---|---|
| EP | 1 220 340 A2 | 7/2002 |
| EP | 1 777 229 A1 | 4/2007 |
| EP | 2 256 840 A2 | 12/2010 |
| JP | 2002-289352 | 10/2002 |
| JP | 2002-302757 | 10/2002 |
| JP | 2002-313583 | 10/2002 |
| JP | 2002-317262 | 10/2002 |
| JP | 2002-319492 | 10/2002 |
| JP | 2003-92185 | 3/2003 |
| JP | 2003-100461 | 4/2003 |
| JP | 2006-318935 | 11/2006 |
| JP | 2007-137872 | 6/2007 |
| JP | 2007-208102 | 8/2007 |
| JP | 2007-287676 | 11/2007 |
| JP | 2008-69221 | 3/2008 |
| JP | 2008-74921 | 4/2008 |

(Continued)

OTHER PUBLICATIONS

Machine translation of JP 2008-074921 A (Apr. 2008).*

(Continued)

*Primary Examiner* — Marie R. Yamnitzky

(74) *Attorney, Agent, or Firm* — Husch Blackwell LLP

(57) ABSTRACT

An organometallic complex emitting blue phosphorescence which can be manufactured inexpensively is provided. An organometallic complex in which nitrogen at the 1-position of a 5-aryl-4H-1,2,4-triazole derivative is coordinated to a Group 9 metal or a Group 10 metal, the aryl group is bonded to the Group 9 metal or the Group 10 metal, and the 5-aryl-4H-1,2,4-triazole derivative is a 3-aryl-5,6,7,8-tetrahydro-4H-[1,2,4]triazolo[4,3-a]pyridine derivative is provided. The organometallic complex emits green to blue phosphorescence and has a cost advantage.

11 Claims, 13 Drawing Sheets

(56) References Cited

FOREIGN PATENT DOCUMENTS

| | | |
|---|---|---|
| JP | 2008-166745 | 7/2008 |
| JP | 2008-308490 | 12/2008 |
| JP | 2009-88491 | 4/2009 |
| JP | 2009-167173 | 7/2009 |
| JP | 2010-77124 | 4/2010 |
| JP | 2010-254679 | 11/2010 |
| WO | WO 2007/049461 A1 | 3/2007 |
| WO | WO 2008/035664 A1 | 3/2008 |
| WO | WO 2008/069153 A1 | 6/2008 |
| WO | WO 2008/143019 A1 | 11/2008 |
| WO | WO 2009/081718 A1 | 7/2009 |
| WO | WO 2009/107497 A1 | 9/2009 |

OTHER PUBLICATIONS

Van Diemen, J.H. et al., "Synthesis and Characterization of Orthometalated Rhodium (III) Complexes Containing Substituted Triazoles," Inorganic Chemistry, vol. 30, No. 21, 1991, pp. 4038-4043, American Chemical Society.

Zamora, F. et al., "Synthesis of Several Palladium Complexes Derived from 2,5-diphenyl-1,3,4-Oxadiazole. Reactivity Against Nucleobase Models,", Journal of Inorganic Biochemistry, vol. 68, No. 4, Dec. 1, 1997, pp. 257-263.

Baldo, M.A. et al., "Very High-Efficiency Green Organic Light-Emitting Devices Based on Electrophosphorescence," Applied Physics Letters, vol. 75, No. 1, Jul. 5, 1999, pp. 4-6.

Liu, J. et al., "Green-Yellow Electrophosphorescence from di [2,5-diphenyl-1,3,4-oxadiazole $C^{2'}$, $N^3$] Platinum(II) Doped PVK Devices," Chinese Physics Letters, vol. 22, No. 3, 2005, pp. 723-726.

Wu, Z.L. et al., "Synthesis and Photoluminescence of a Novel Iridium Complex (BuPhOXD)2Ir(acac) with Unit of 1,3,4-Oxadiazole," Chinese Chemical Letters, vol. 16, No. 2, 2005, pp. 241-244.

Chen, L. et al., "Synthesis, Structure, Electrochemistry, Photophysics and Electroluminescence of 1,3,4-Oxadiazole-Based Ortho-Metalated Iridium(III) Complexes,", Journal of Organometallic Chemistry, vol. 691, No. 16, Aug. 1, 2006, pp. 3519-3530.

Lo, S.-C. et al., "Blue Phosphorescence from Iridium(III) Complexes at Room Temperature," Chemistry of Materials, vol. 18, No. 21, 2006, pp. 5119-5129, American Chemical Society.

Notification re Japanese application No. JP 2012-146604, dated Mar. 19, 2013 (with English translation).

* cited by examiner

ORGANOMETALLIC COMPLEX, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

The present invention relates to a novel organometallic complex that is capable of converting triplet excited energy into luminescence. In addition, the present invention relates to a light-emitting element, a light-emitting device, an electronic device, and a lighting device each using the organometallic complex.

2. Description of the Related Art

In recent years, a light-emitting element using a light-emitting organic compound or inorganic compound as a light-emitting material has been actively developed. In particular, a light-emitting element called an EL (electroluminescence) element has attracted attention as a next-generation flat panel display element because it has a simple structure in which a light-emitting layer containing a light-emitting material is provided between electrodes, and characteristics such as feasibility of being thin, lightweight, and highly responsive to input signals, and able to be driven with direct current at a low voltage. In addition, a display using such a light-emitting element has a feature that it is excellent in contrast and image quality, and has a wide viewing angle. Further, since such a light-emitting element is a plane light source, the light-emitting element is considered to be applicable to a light source such as a backlight of a liquid crystal display and lighting.

In the case where the light-emitting substance is an organic compound having a light-emitting property, the emission mechanism of the light-emitting element is a carrier-injection type. That is, by applying a voltage with a light-emitting layer interposed between electrodes, electrons and holes injected from the electrodes, recombine to put the light-emitting substance into an excited state, and light is emitted when the light-emitting substance returns to a ground state from the excited state. There are two types of the excited states: a singlet excited state (S*) and a triplet excited state (T*). In addition, the statistical generation ratio thereof in a light-emitting element is considered to be S*:T*=1:3.

In general, the ground state of a light-emitting organic compound is a singlet state. In light emission from a singlet excited state (S*), electron transition occurs between the same spin multiplicities. This is called fluorescence. In contrast, in light emission from a triplet excited state (T*), electron transition occurs between different spin multiplicities. This is called phosphorescence. Thus, in a compound emitting fluorescence (hereinafter referred to as fluorescent compound), in general, phosphorescence is not observed at room temperature, and only fluorescence is observed. Accordingly, the internal quantum efficiency (the ratio of generated photons to injected carriers) in a light-emitting element using a fluorescent compound is assumed to have a theoretical limit of 25% based on S*:T*=1:3.

In contrast, internal quantum efficiency in a light-emitting element using a compound emitting phosphorescence (hereinafter referred to as phosphorescent compound) can be 100% in theory when light emission led from intersystem crossing from a singlet excited state to a triplet excited state is taken into account. For this reason, the light-emitting element using a phosphorescent compound has been actively developed in recent years in order to achieve a highly efficient light-emitting element.

As a phosphorescent compound, an organometallic complex having iridium as a central metal has attracted attention. Development has enabled phosphorescent compounds to emit light with various wavelengths from red to blue; however, for phosphorescence, i.e., light emission from a triplet level which is lower than a singlet excited level in terms of energy, a phosphorescent compound having an extremely wide energy gap is necessary for obtaining green to blue light emission with large energy. Such substances are difficult to develop and the number thereof is still limited.

Patent Document 1 discloses, as a phosphorescent compound emitting phosphorescence with a short wavelength, an iridium complex in which an imidazole derivative is a ligand.

[Reference]

[Patent Document]

[Patent Document 1] PCT International Publication No. 2007/029461

SUMMARY OF THE INVENTION

In view of practical use of light-emitting elements using a blue phosphorescent material, cost of the material itself also becomes a problem. Especially in a field of lighting including incandescent lamps, fluorescent lamps, and the like, which fowls a mature market, competitiveness in terms of cost is of extreme importance.

In view of the foregoing, an object of the present invention is to provide an organometallic complex exhibiting blue phosphorescence which can be manufactured at low cost.

Further, it is another object of the present invention to provide a light-emitting element which can be fabricated at low cost and which highly efficiently emits light in the wavelength region of blue-green to blue, by the use of such an organometallic complex. Moreover, it is a further object to provide an inexpensive light-emitting device, an inexpensive electronic device, and an inexpensive lighting device each using the light-emitting element.

The present inventors have found that an organometallic complex in which nitrogen at the 1-position of a 5-aryl-4H-1,2,4-triazole derivative is coordinated to a Group 9 metal or a Group 10 metal, the aryl group is bonded to the Group 9 metal or the Group 10 metal, and the 5-aryl-4H-1,2,4-triazole derivative is 3-aryl-5,6,7,8-tetrahydro-4H-[1,2,4]triazolo[4,3-a]pyridine derivative emits phosphorescence. Specifically, the present inventors have found that a tris-type organometallic complex in which the metal is iridium exhibits green to blue phosphorescence and has a cost advantage.

Further, the present inventors have found that a light-emitting element including the above-described organometallic complex between a pair of electrodes emits light in the wavelength region of blue highly efficiently by application of a voltage, and can be provided at low cost.

Thus, one embodiment of the present invention is an organometallic complex in which a 5-aryl-4H-1,2,4-triazole derivative is a ligand and iridium is a central metal. Specifically, one embodiment of the present invention is an organometallic complex represented by General Formula (G1).

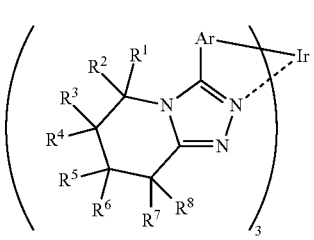

(G1)

Another embodiment of the present invention is an organometallic complex represented by General Formula (G2).

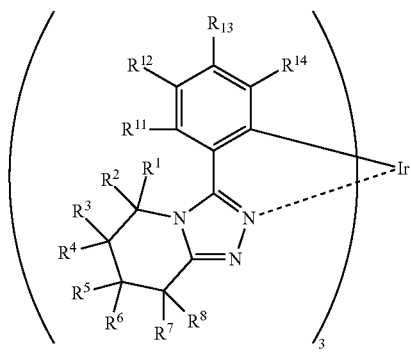

(G2)

A further embodiment of the present invention is an organometallic complex represented by General Formula (G3).

(G3)

In General Formula (G1), Ar represents a substituted or unsubstituted phenylene group or a substituted or unsubstituted naphthylene group. In General Formula (G2), $R^{11}$ to $R^{14}$ separately represent any of hydrogen, an alkyl group having 1 to 4 carbon atoms, an alkoxy group having 1 to 4 carbon atoms, an alkylthio group having 1 to 4 carbon atoms, a haloalkyl group having 1 to 4 carbon atoms, a halogeno group, and a phenyl group.

In General Formulae (G1); (G2), and (G3), $R^1$ to $R^8$ separately represent hydrogen or an alkyl group having 1 to 4 carbon atoms. Note that an intramolecular bridge structure may also be comprised in the organometallic complexes represented by General Formulae (G1), (G2), and (G3).

Note that an organometallic complex in which $R^1$ to $R^8$ and $R^{11}$ to $R^{14}$ are all hydrogen has a cost advantage because its raw materials are easy to obtain and less expensive.

In view of the above, a still further embodiment of the present invention is an organometallic complex represented by Structural Formula (100) below.

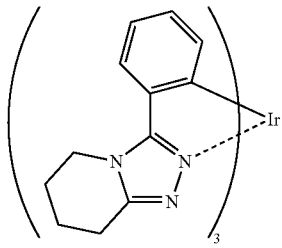

(100)

A yet still further embodiment of the present invention is a light-emitting element including, between a pair of electrodes, any of the organometallic complexes described above. In particular, any of the organometallic complexes described above is preferably contained in a light-emitting layer.

A light-emitting device, an electronic device, and a lighting device each using the above light-emitting element also belong to the category of the present invention. Note that the light-emitting device in this specification includes, in its category, an image display device, a light-emitting device, and a light source. In addition, the light-emitting device includes, in its category, all of a module in which a connector such as a flexible printed circuit (FPC), a tape automated bonding (TAB) tape or a tape carrier package (TCP) is connected to a panel, a module in which a printed wiring board is provided on the tip of a TAB tape or a TCP, and a module in which an integrated circuit (IC) is directly mounted on a light-emitting element by a chip on glass (COG) method.

According to one embodiment of the present invention, an organometallic complex which exhibits phosphorescence in the wavelength region of green to blue and is advantageous in terms of cost can be provided.

According to one embodiment of the present invention, a light-emitting element which can be fabricated at low cost and which highly efficiently emits light in the wavelength region of blue-green to blue can be provided. In addition, an inexpensive light-emitting device, an inexpensive electronic device, and an inexpensive lighting device each using the light-emitting element can be provided.

According to one embodiment of the present invention, a light-emitting element using the organometallic complex, and a light-emitting device, an electronic device, and a lighting device each using the light-emitting element can be provided.

DETAILED DESCRIPTION OF THE INVENTION

Figure 1:
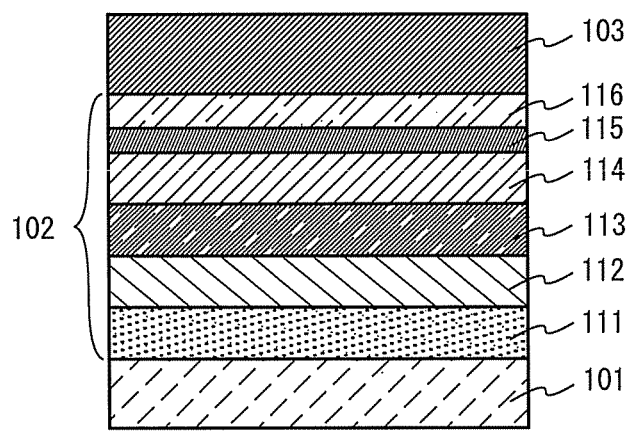
FIG. 1 illustrates a light-emitting element of one embodiment of the present invention.

Embodiments will now be described with reference to drawings in detail. Note that the invention is not limited to the following description, and it will be easily understood by those skilled in the art that various changes and modifications can be made without departing from the spirit and scope of the invention. Therefore, the invention should not be construed as being limited to the description in the following embodiments. Note that in the structures of the invention described below, the same portions or portions having similar functions are denoted by the same reference numerals in different drawings, and description of such portions is not repeated.

(Embodiment 1)

In this embodiment, an organometallic complex of one embodiment of the present invention is described.

An organometallic complex in this embodiment is an organometallic complex in which a 5-aryl-4H-1,2,4-triazole derivative is a ligand. When a central metal of the organometallic complex is a Group 9 metal or a Group 10 metal, phosphorescence is obtained. In particular, an organometallic complex in which the central metal is iridium is preferable because of its favorable phosphorescence quantum yield. Note that a tris-type organometallic complex is preferable because phosphorescence with a shorter wavelength can be easily obtained.

The 5-aryl-4H-1,2,4-triazole derivative as the ligand is a 3-aryl-5,6,7,8-tetrahydro-4H-[1,2,4]triazolo[4,3-a]pyridine derivative. The 5-aryl-4H-1,2,4-triazole derivative involves fewer synthesis steps, is easily synthesized, and is thus advantageous in cost. In addition, the 5-aryl-4H-1,2,4-triazole derivative is advantageous also in yield because complex formation reaction relatively easily proceeds, and the cost can be further reduced.

An organometallic complex having the above structure emits blue-green to blue phosphorescence and can be manufactured inexpensively; thus, the organometallic complex is advantageous in cost.

More specifically, an organometallic complex having the above structure according to this embodiment is represented by General Formula (G1) below.

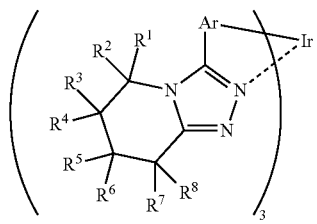

(G1)

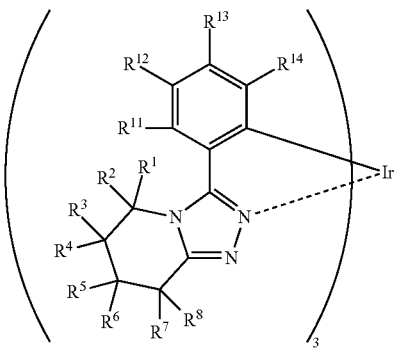

(G2)

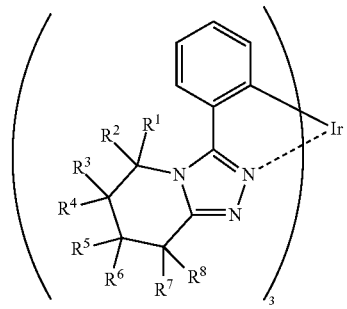

(G3)

In General Formula (G1), Ar represents a substituted or unsubstituted phenylene group or a substituted or unsubstituted naphthylene group. In the case where Ar has a substituent, an alkyl group having 1 to 4 carbon atoms, an alkoxy group having 1 to 4 carbon atoms, an alkylthio group having 1 to 4 carbon atoms, a haloalkyl group having 1 to 4 carbon atoms, a halogeno group, a phenyl group, and the like can be given as the substituent. More specifically, a methyl group, an ethyl group, a propyl group, an isopropyl group, a butyl group, a sec-butyl group, an isobutyl group, a tert-butyl group, a methoxy group, an ethoxy group, a propoxy group, an isopropoxy group, a butoxy group, a sec-butoxy group, an isobutoxy group, a tert-butoxy group, a methylsulfinyl group, an ethylsulfinyl group, a propylsulfinyl group, an isopropylsulfinyl group, a butylsulfinyl group, an isobutylsulfinyl group, a sec-butylsulfinyl group, a tert-butylsulfinyl group, a fluoro group, a fluoromethyl group, a difluoromethyl group, a trifluoromethyl group, a chloro group, a chloromethyl group, a dichloromethyl group, a trichloromethyl group, a bromomethyl group, a 2,2,2-trifluoroethyl group, a 3,3,3-trifluoropropyl group, a 1,1,1,3,3,3-hexafluoroisopropyl group, or the like can be employed.

In General Formula (G2), $R^{11}$ to $R^{14}$ separately represent any of hydrogen, an alkyl group having 1 to 4 carbon atoms, au alkoxy group having 1 to 4 carbon atoms, an alkylthio group having 1 to 4 carbon atoms, a haloalkyl group having 1 to 4 carbon atoms, a halogeno group, and a phenyl group. Specific examples of $R^{11}$ to $R^{14}$ are hydrogen, a methyl group, an ethyl group, a propyl group, an isopropyl group, a butyl group, a sec-butyl group, an isobutyl group, a tert-butyl group, a methoxy group, an ethoxy group, a propoxy group, an isopropoxy group, a butoxy group, a sec-butoxy group, an isobutoxy group, a tert-butoxy group, a methylsulfinyl group, an ethylsulfinyl group, a propylsulfinyl group, an isopropylsulfinyl group, a butylsulfinyl group, an isobutylsulfinyl group, a sec-butylsulfinyl group, a tert-butylsulfinyl group, a fluoro group, a fluoromethyl group, a difluoromethyl group, a trifluoromethyl group, a chloro group, a chloromethyl group, a dichloromethyl group, a trichloromethyl group, a bromomethyl group, a 2,2,2-trifluoroethyl group, a 3,3,3-trifluoropropyl group, a 1,1,1,3,3,3-hexafluoroisopropyl group, and the like.

Further, in General Formulae (G1), (G2), and (G3), $R^1$ to $R^8$ separately represent hydrogen or an alkyl group having 1 to 4 carbon atoms. Specific examples of $R^1$ to $R^8$ are hydrogen, a methyl group, an ethyl group, a propyl group, an isopropyl group, a butyl group, a sec-butyl group, an isobutyl group, and a tert-butyl group. Note that carbon atoms facing each other may share a divalent substituent to four a ring.

Note that an organometallic complex in which $R^1$ to $R^8$ and $R^{11}$ to $R^{14}$ are all hydrogen has a cost advantage because its raw materials are easy to obtain and less expensive.

Next, an example of a method of synthesizing an organometallic complex in this embodiment is described.

<Method of Synthesizing a 5-aryl-4H-1,2,4-triazole Derivative Represented by General Formula (G0)>

First, an example of a method of synthesizing a 5-aryl-4H-1,2,4-triazole derivative represented by General Formula (G0) below is described.

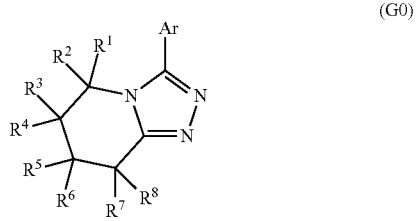

(G0)

In General Formula (G0), Ar represents a substituted or unsubstituted phenylene group or a substituted or unsubstituted naphthylene group. In the case where Ar has a substituent, an alkyl group having 1 to 4 carbon atoms, an alkoxy group having 1 to 4 carbon atoms, an alkylthio group having 1 to 4 carbon atoms, a haloalkyl group having 1 to 4 carbon atoms, a halogeno group, a phenyl group, and the like can be given as the substituent. Further, $R^1$ to $R^8$ separately represent hydrogen or an alkyl group having 1 to 4 carbon atoms.

For example, as shown in the diagram (a) below, the 5-aryl-4H-1,2,4-triazole derivative represented by General Formula (G0) can be obtained when aryl hydrazide (A1) and an O-methyl valerolactam derivative (A2) react with each other.

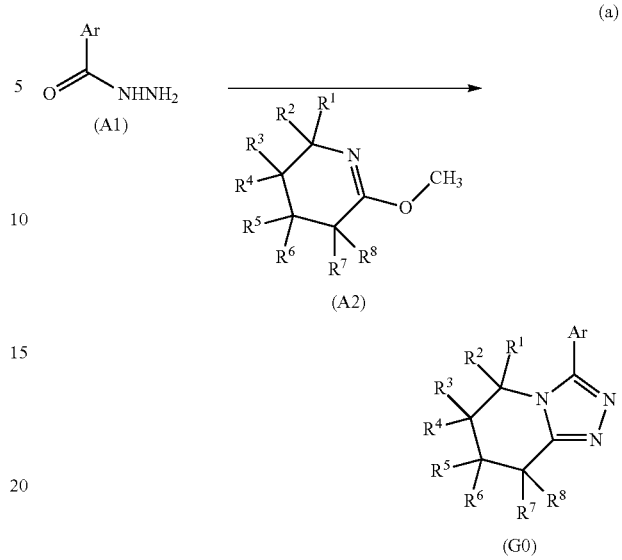

In (A1) in the above formula, Ar represents a substituted or unsubstituted phenylene group or a substituted or unsubstituted naphthylene group and in (A2), $R^1$ to $R^8$ separately represent hydrogen or an alkyl group having 1 to 4 carbon atoms.

Note that various kinds of the above-described compounds (A1) and (A2) are commercially available or can be synthesized. In this manner, various types of the 5-aryl-4H-1,2,4-triazole derivative represented by General Formula (G0) can be synthesized. Thus, an organometallic complex of one embodiment of the present invention which is represented by General Formula (G1) features abundant variations in ligands. By using such an organometallic complex having wide variations of a ligand in manufacture of a light-emitting element, fine adjustment of element characteristics required for the light-emitting element can be performed easily.

<Method of Synthesizing an Organometallic Complex of One Embodiment of the Present Invention, Represented by General Formula (G1)>

The organometallic complex of one embodiment of the invention, represented by General Formula (G1), can be synthesized by the synthesis diagram (b) below. That is, the 5-aryl-4H-1,2,4-triazole derivative represented by General Formula (G0) is mixed with an iridium compound which contains a halogen (e.g., iridium chloride, iridium bromide, or iridium iodide) or with an iridium organometallic complex compound (e.g., an acetylacetonate complex or a diethylsulfide complex) and the mixture is then heated, so that the organometallic complex represented by General Formula (G1) can be obtained. Further, this heating process may be performed after the 5-aryl-4H-1,2,4-triazole derivative represented by General Formula (G0) and the iridium compound which contains a halogen or the iridium organometallic complex compound are dissolved in an alcohol-based solvent (e.g., glycerol, ethylene glycol, 2-methoxyethanol, or 2-ethoxyethanol). There is no particular limitation on a heating means, and an oil bath, a sand bath, or an aluminum block may be used. Alternatively, microwaves can be used as a heating means.

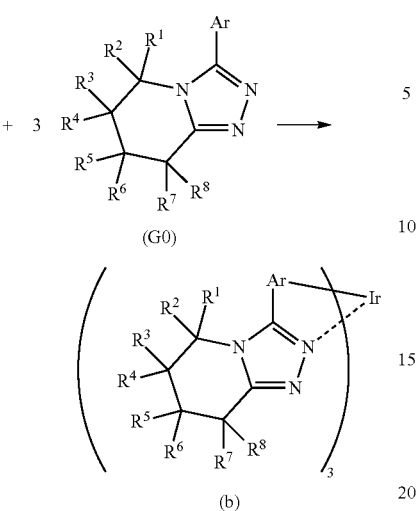

(G0)

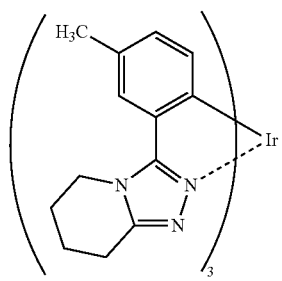

(b)

In the diagram (b), Ar represents a substituted or unsubstituted phenylene group or a substituted or unsubstituted naphthylene group. In the case where Ar has a substituent, an alkyl group having 1 to 4 carbon atoms, an alkoxy group having 1 to 4 carbon atoms, an alkylthio group having 1 to 4 carbon atoms, a haloalkyl group having 1 to 4 carbon atoms, a halogeno group, a phenyl group, and the like can be given as the substituent. Further, $R^1$ to $R^8$ separately represent hydrogen or an alkyl group having 1 to 4 carbon atoms.

As specific examples of organometallic complexes represented by General Formula (G1), organometallic complexes represented by Structural Formulae (100) to (124) can be given. Note that the present invention is not limited to the organometallic complexes represented by these structural formulae. In addition, Structural Formulae (121) to (124) illustrate examples of organometallic complexes in which a ligand comprises an intramolecular bridge structure.

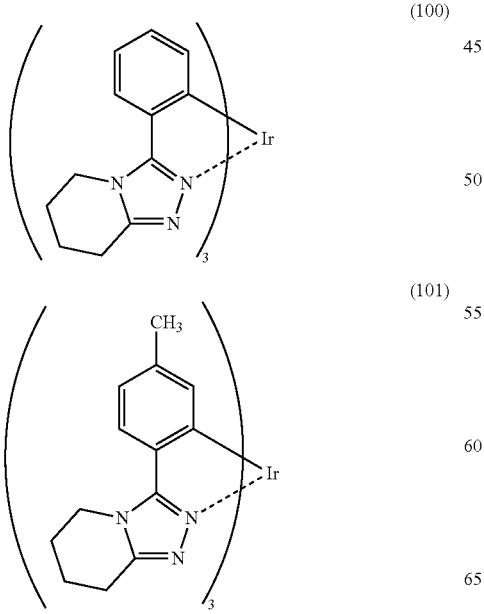

(100)

(101)

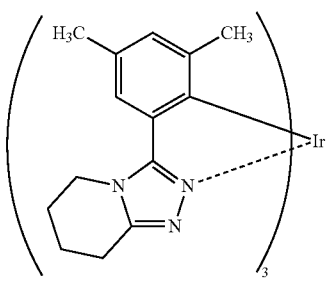

(102)

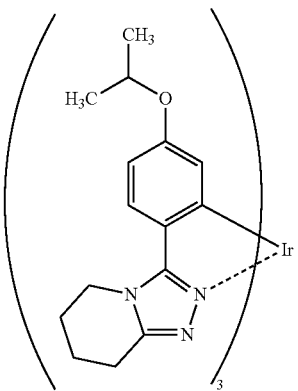

(103)

(104)

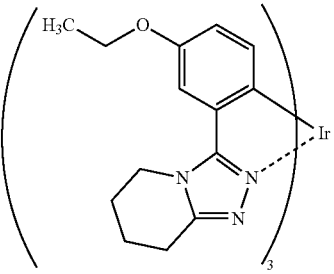

(105)

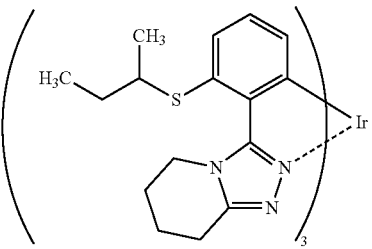

(106)

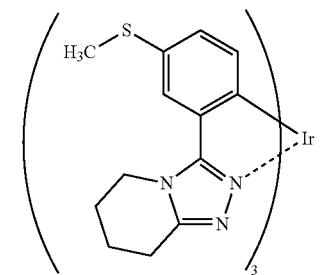 (107)
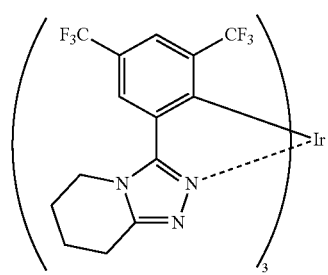 (108)
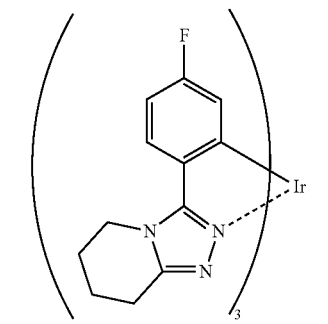 (109)
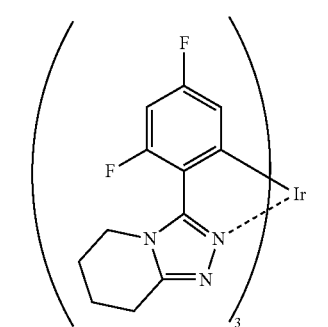 (110)
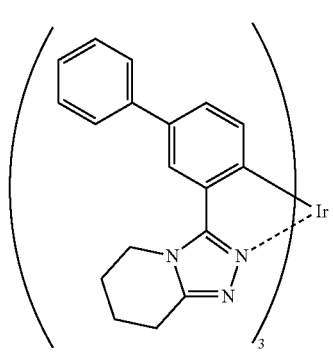 (111)
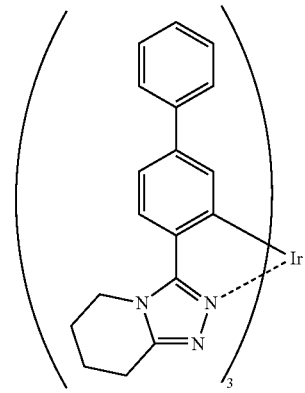 (112)
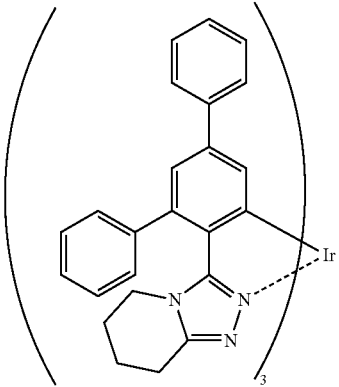 (113)
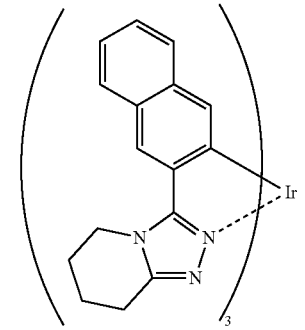 (114)
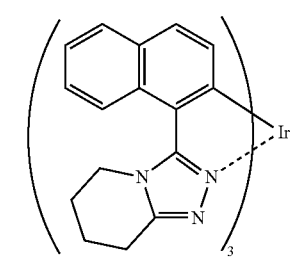 (115)
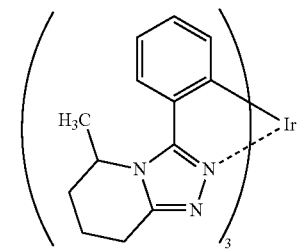 (116)

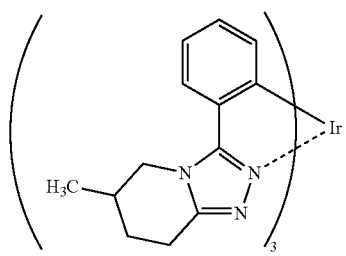 (117)

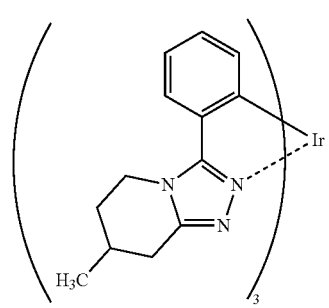 (118)

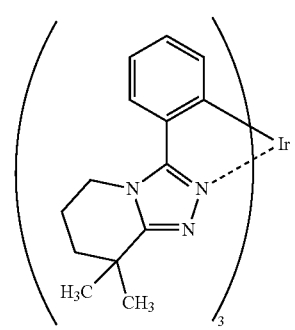 (119)

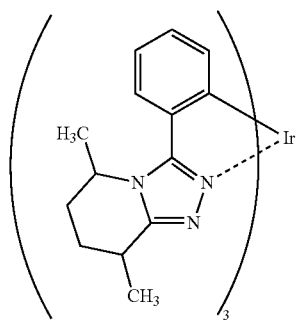 (120)

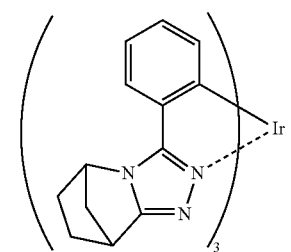 (121)

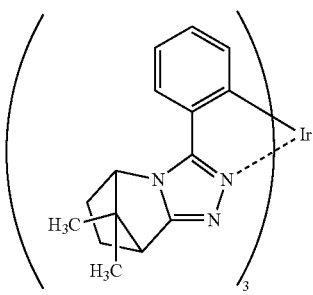 (122)

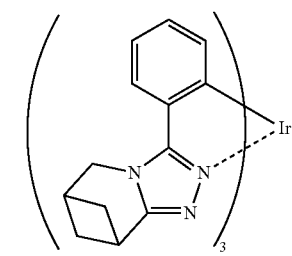 (123)

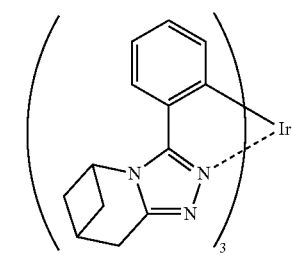 
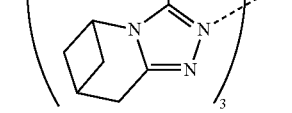 (124)

Depending on the type of the ligand, there can be stereoisomers of the organometallic complexes represented by Structural Formulae (100) to (124) above, and such isomers are included in the category of an organometallic complex of one embodiment of the present invention.

The above-described organometallic complexes each of which is one embodiment of the present invention are novel substances capable of emitting blue phosphorescence. Further, the above organometallic complexes can be manufactured inexpensively.

This embodiment can be implemented in an appropriate combination with the other embodiments.

(Embodiment 2)

In this embodiment, a light-emitting element using the organometallic complex which is described in Embodiment 1 as one embodiment of the present invention is described. Specifically, a light-emitting element in which the organometallic complex is used for a light-emitting layer is described with reference to FIG. 1.

In a light-emitting element described in this embodiment, as illustrated in FIG. 1, an EL layer 102 including a light-emitting layer 113 is provided between a pair of electrodes (a first electrode 101 and a second electrode 103), and the EL layer 102 includes a hole-injection layer 111, a hole-transport layer 112, an electron-transport layer 114, an electron-injection layer 115, a charge-generation layer 116, and the like in addition to the light-emitting layer 113.

In this embodiment, the first electrode 101 functions as an anode, and the second electrode 103 functions as a cathode. Note that when at least one of the first electrode 101 and the second electrode 103 has a light-transmitting property, light emitted from the EL layer 102 can be extracted to the outside to be used.

By application of a voltage to such a light-emitting element, holes injected from the first electrode 101 side and electrons injected from the second electrode 103 side recombine in the light-emitting layer 113 to raise the organometallic complex to an excited state. Then, light is emitted when the organometallic complex in the excited state returns to the ground state. Thus, the organometallic complex of one embodiment of the present invention functions as a light-emitting substance in the light-emitting element.

Note that the hole-injection layer 111 in the EL layer 102 is a layer containing a substance with a high hole-injection property, or a layer including a composite material containing a substance with a high hole-transport property and an acceptor substance. When the hole-injection layer is a layer including the composite material, electrons are extracted from the substance with a high hole-transport property by the acceptor substance and thus holes are generated. Thus, holes are injected from the hole-injection layer 111 into the light-emitting layer 113 through the hole-transport layer 112.

The charge-generation layer 116 is a layer containing a substance having a high hole-transport property and an acceptor substance. Electrons are extracted from the substance having a high hole-transport property by the acceptor substance, and the extracted electrons are injected from the electron-injection layer 115 having an electron-injection property into the light-emitting layer 113 through the electron-transport layer 114.

A specific example in which the light-emitting element described in this embodiment is manufactured is described.

As the first electrode 101 and the second electrode 103, a metal, an alloy, an electrically conductive compound, a mixture thereof, and the like can be used.

It is preferred that the first electrode 101 as the anode be formed using any of metals, alloys, and conductive compounds with a high work function (specifically, 4.0 eV or higher), a mixture thereof, or the like. Specifically, for example, indium oxide-tin oxide (ITO: indium tin oxide), indium oxide-tin oxide containing silicon or silicon oxide, indium oxide-zinc oxide (indium zinc oxide), indium oxide containing tungsten oxide and zinc oxide (IWZO), or the like is given. Films of such conductive metal oxide are generally formed by a sputtering method. For example, indium oxide-zinc oxide can be formed by a sputtering method using a target obtained by adding 1 wt % to 20 wt % of zinc oxide to indium oxide. Moreover, indium oxide (IWZO) including tungsten oxide and zinc oxide can be formed by a sputtering method using a target in which 0.5 wt % to 5 wt % of tungsten oxide and 0.1 wt % to 1 wt % of zinc oxide with respect to indium oxide are included. Note that instead of a sputtering method, a sol-gel method can be applied and used to form the first electrode 101. Besides, as a material used for the first electrode 101, the following can be given: gold (Au), platinum (Pt), nickel (Ni), tungsten (W), chromium (Cr), molybdenum (Mo), iron (Fe), cobalt (Co), copper (Cu), palladium (Pd), a nitride of a metal material (e.g., titanium nitride), and the like. Graphene can also be used.

For the cathode, any of metals, alloys, electrically conductive compounds, and mixtures thereof which have a low work function (specifically, a work function of 3.8 eV or less) or the like can be used. Specific examples of such a cathode material include elements that belong to Groups 1 and 2 of the periodic table such as lithium (Li), cesium (Cs), magnesium (Mg), calcium (Ca), and strontium (Sr), alloys thereof (e.g., MgAg or AlLi), rare earth metals such as europium (Eu) and ytterbium (Yb), alloys thereof, and the like. Any of a variety of conductive materials such as Al, Ag, ITO, indium oxide-tin oxide containing silicon, or silicon oxide can be used for the cathode regardless of a work function when comprised in a stacked layer including a film of an alkali metal compound, an alkaline earth metal compound, or a rare earth metal compound (e.g., lithium fluoride (LiF), lithium oxide (LiOx), cesium fluoride (CsF), calcium fluoride ($CaF_2$), or erbium fluoride ($ErF_3$)). Films of these conductive materials can be formed by a sputtering method, an ink-jet method, a spin coating method, or the like.

The hole-injection layer 111 is a layer which is provided in contact with an anode and contains a substance having a high hole-injection property. The hole-injection layer 111 can be formed using molybdenum oxide, vanadium oxide, ruthenium oxide, tungsten oxide, manganese oxide, or the like. Alternatively, the hole-injection layer 111 can be formed using a phthalocyanine-based compound such as phthalocyanine (abbreviation: $H_2Pc$) or copper phthalocyanine (abbreviation: CuPc); an aromatic amine compound such as 4,4'-bis[N-(4-diphenylaminophenyl)-N-phenylamino]biphenyl (abbreviation: DPAB) or N,N'-bis[4-[bis(3-methylphenyl)amino]phenyl]-N,N'-diphenyl-[1,1'-biphenyl]-4,4'-diamine (abbreviation: DNTPD); a high molecule such as poly(ethylenedioxythiophene)/poly(styrenesulfonic acid) (PEDOT/PSS); or the like.

Alternatively, the hole-injection layer 111 can be formed using a composite material in which a substance exhibiting an acceptor property with respect to a substance having a high hole-transport property is contained in the substance having a high hole-transport property. Note that when the composite material in which a substance exhibiting an acceptor property is contained in a substance having a high hole-transport property is provided in contact with the anode, a material for forming the anode can be selected regardless of its work function. In other words, besides a material with a high work function, a material with a low work function may also be used for the anode. As the substance exhibiting an acceptor property, 7,7,8,8-tetracyano-2,3,5,6-tetrafluoroquinodimethane (abbreviation: $F_4$-TCNQ), chloranil, and the like are given. In addition, a transition metal oxide is given. Moreover, oxides of metals that belong to Group 4 to Group 8 of the periodic table can also be used. Specifically, vanadium oxide, niobium oxide, tantalum oxide, chromium oxide, molybdenum oxide, tungsten oxide, manganese oxide, and rhenium oxide are preferable because their electron-accepting property is high. Among these, molybdenum oxide is especially preferable because it is stable in the air, has a low hygroscopic property, and is easily handled.

As the substance having a high hole-transport property used for the composite material, any of a variety of compounds such as an aromatic amine compound, a carbazole derivative, an aromatic hydrocarbon, and a high molecular compound (e.g., an oligomer, a dendrimer, or a polymer) can be used. The organic compound used for the composite material is preferably an organic compound having a high hole-transport property. Specifically, a substance having a hole mobility of $10^{-6}$ $cm^2/Vs$ or higher is preferably used. However, another substance may be used instead of the above described materials as long as the substance has a hole-transport property higher than an electron-transport property. The organic compounds that can be used for the composite material are specifically given below.

As the aromatic amine compounds, for example, there are N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis[4-[bis(3-methylphenyl)amino]phenyl]-N,N'-diphenyl-[1,1'- biphenyl]-4,4'-diamine (abbreviation: DNTPD), and 1,3,5-tris[N-(4-diphenylaminophenyl)-N-phenylamino]benzene (abbreviation: DPA3B).

As the carbazole derivatives which can be used for the composite material, the followings are given specifically: 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); 3-[N-(1-naphthyl)-N-(9-phenylcarbazol-3-yl)amino]-9-phenylcarbazole (abbreviation: PCzPCN1); and the like.

Other examples of the carbazole derivatives which can be used for the composite material include 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), and 1,4-bis[4-(N-carbazolyl)phenyl]-2,3,5,6-tetraphenylbenzene.

Examples of the aromatic hydrocarbon which can be used for the composite material include 2-tert-butyl-9,10-di(2-naphthyl)anthracene (abbreviation: t-BuDNA); 2-tert-butyl-9,10-di(1-naphthyl)anthracene; 9,10-bis(3,5-diphenylphenyl)anthracene (abbreviation: DPPA); 2-tert-butyl-9,10-bis(4-phenylphenyl)anthracene (abbreviation: t-BuDBA); 9,10-di(2-naphthyl)anthracene (abbreviation: DNA); 9,10-diphenylanthracene (abbreviation: DPAnth); 2-tert-butylanthracene (abbreviation: t-BuAnth); 9,10-bis(4-methyl-1-naphthyl)anthracene (abbreviation: DMNA); 2-tert-butyl-9,10-bis[2-(1-naphthyl)phenyl]anthracene; 9,10-bis[2-(1-naphthyl)phenyl]anthracene; 2,3,6,7-tetramethyl-9,10-di(1-naphthyl)anthracene; 2,3,6,7-tetramethyl-9,10-di(2-naphthyl)anthracene; 9,9'-bianthryl; 10,10'-diphenyl-9,9'-bianthryl; 10,10'-bis(2-phenylphenyl)-9,9'-bianthryl; 10,10'-bis[(2,3,4,5,6-pentaphenyl)phenyl]-9,9'-bianthryl; anthracene; tetracene; rubrene; perylene; and 2,5,8,11-tetra(tert-butyl)perylene. Besides those; pentacene, coronene, or the like can be used. In particular, the aromatic hydrocarbon which has a hole mobility of $1\times10^{-6}$ cm$^2$/Vs or higher and which has 14 to 42 carbon atoms is particularly preferable.

The aromatic hydrocarbon which can be used for the composite material may have a vinyl skeleton. As the aromatic hydrocarbon having a vinyl group, 4,4'-bis(2,2-diphenylvinyl)biphenyl (abbreviation: DPVBi) and 9,10-bis[4-(2,2-diphenylvinyl)phenyl]anthracene (abbreviation: DPVPA) are given, for example.

Moreover, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacrylamide] (abbreviation: PTPDMA), or poly[N,N'-bis(4-butylphenyl)-N,N'-bis(phenyl)benzidine (abbreviation: Poly-TPD) can also be used.

Note that a layer formed using such a composite material can be very suitably used for optical design that is performed to control the light extraction efficiency, directivity, or the like of light emitted from the light-emitting layer 113 because the drive voltage hardly varies even when the layer formed using the composite material is formed to be thick or thin.

The hole-transport layer 112 is formed using a substance with a high hole-transport property. As a substance with a high hole-transport property, for example, aromatic amine compounds such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4',4''-tris(N,N-diphenylamino)triphenylamine (abbreviation: TDATA), 4,4',4''-tris[N-(3-methyl-phenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), and 4-phenyl-4'-(9-phenylfluoren-9-yl)triphenylamine (abbreviation: BPAFLP) can be used. The substances mentioned here are mainly ones that have a hole mobility of $10^{-6}$ cm$^2$/Vs or higher. Any of the organic compounds given above as examples of the substance having a high hole-transport property in the composite material can also be used for the hole-transport layer 112. However, another substance may be used instead of the above described materials as long as the substance has a hole-transport property higher than an electron-transport property. The layer containing a substance with a high hole-transport property is not limited to a single layer, and a stacked layer in which two or more layers containing any of the above-described substances are stacked may be used.

Further, for the hole-transport layer 112, a high molecular compound such as poly(N-vinylcarbazole) (abbreviation: PVK), or poly(4-vinyltriphenylamine) (abbreviation: PVTPA) can be used.

The light-emitting layer 113 contains the organometallic complex described in Embodiment 1 as a guest material serving as a light-emitting substance and a substance that has higher triplet excitation energy than this organometallic complex as a host material.

Preferable examples of the substance (i.e., host material) used for dispersing any of the above-described organometallic complexes include: any of compounds having an arylamine skeleton, such as 2,3-bis(4-diphenylaminophenyl)quinoxaline (abbreviation: TPAQn) and NPB, carbazole derivatives such as CBP and 4,4',4''-tris(N-carbazolyl)triphenylamine (abbreviation: TCTA), and metal complexes such as bis[2-(2-hydroxyphenyl)pyridinato]zinc (abbreviation: Znpp$_2$), bis[2-(2-hydroxyphenyl)benzoxazolato]zinc (abbreviation: Zn(BOX)$_2$), bis(2-methyl-8-quinolinolato)(4-phenylphenolato)aluminum (abbreviation: BAlq), and tris(8-quinolinolato)aluminum (abbreviation: Alq$_3$). Alternatively, a high molecular compound such as PVK can be used.

Note that in the case where the light-emitting layer 113 contains the above-described organometallic complex (guest material) and the host material, green to blue phosphorescence with high emission efficiency can be obtained from the light-emitting layer 113.

The electron-transport layer 114 is a layer containing a substance having a high electron-transport property. For the electron-transport layer 114, metal complexes such as Alq$_3$, tris(4-methyl-8-quinolinolato)aluminum (abbreviation: Almq$_3$), bis(10-hydroxybenzo[h]quinolinato)beryllium (abbreviation: BeBq$_2$), BAlq, Zn(BOX)$_2$, or bis[2-(2-hydroxyphenyl)benzothiazolato]zinc (abbreviation: Zn(BTZ)$_2$) can be used. Alternatively, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs) can be used. Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used. The substances described here are mainly ones having an electron mobility of $10^{-6}$ cm$^2$/Vs or higher. Note that other than these substances, any substance that has a property of transporting more easily electrons than holes may be used for the electron-transport layer.

Further, the electron-transport layer 114 is not limited to a single layer, and a stacked layer in which two or more layers containing any of the above-described substances are stacked may be used.

The electron-injection layer 115 is a layer containing a substance having a high electron-injection property. For the electron-injection layer 115, an alkali metal, an alkaline earth metal, or a compound thereof, such as lithium fluoride (LiF), cesium fluoride (CsF), calcium fluoride ($CaF_2$), or lithium oxide (LiOx), can be used. Alternatively, a rare earth metal compound such as erbium fluoride ($ErF_3$) can be used. Further alternatively, the substances for forming the electron-transport layer 114, which are described above, can be used.

Alternatively, a composite material in which an organic compound and an electron donor (donor) are mixed may be used for the electron-injection layer 115. Such a composite material is excellent in an electron-injection property and an electron-transport property because electrons are generated in the organic compound by the electron donor. In this case, the organic compound is preferably a material excellent in transporting the generated electrons. Specifically, for example, the substances for forming the electron-transport layer 114 (e.g., a metal complex and a heteroaromatic compound), which are described above, can be used. As the electron donor, a substance showing an electron-donating property with respect to the organic compound may be used. Specifically, an alkali metal, an alkaline earth metal, and a rare earth metal are preferable, and lithium, cesium, magnesium, calcium, erbium, ytterbium, and the like are given. In addition, alkali metal oxide or alkaline earth metal oxide such as lithium oxide, calcium oxide, barium oxide, and the like can be given. A Lewis base such as magnesium oxide can alternatively be used. An organic compound such as tetrathiafulvalene (abbreviation: TTF) can alternatively be used.

Note that each of the above-described hole-injection layer 111, hole-transport layer 112, light-emitting layer 113, electron-transport layer 114, electron-injection layer 115, and charge-generation layer 116 can be formed by a method such as an evaporation method (e.g., a vacuum evaporation method), an ink-jet method, or a coating method.

In the above-described light-emitting element, current flows due to a potential difference generated between the first electrode 101 and the second electrode 103 and holes and electrons recombine in the EL layer 102, whereby light is emitted. Then, the emitted light is extracted outside through one or both of the first electrode 101 and the second electrode 103. Therefore, one or both of the first electrode 101 and the second electrode 103 are electrodes having a light-transmitting property.

The above-described light-emitting element can emit phosphorescence originating from the organometallic complex and thus can have higher efficiency than a light-emitting element using a fluorescent compound.

Note that the light-emitting element described in this embodiment is an example of a light-emitting element manufactured using the organometallic complex that is one embodiment of the present invention. Further, as a light-emitting device including the above light-emitting element, a passive matrix light-emitting device and an active matrix light-emitting device can be manufactured. It is also possible to manufacture a light-emitting device with a microcavity structure including a light-emitting element which is a different light-emitting element from the above light-emitting elements as described in another embodiment. Each of the above light-emitting devices is included in the present invention.

Note that there is no particular limitation on the structure of the TFT in the case of manufacturing the active matrix light-emitting device. For example, a staggered TFT or an inverted staggered TFT can be used as appropriate. Further, a driver circuit formed over a TFT substrate may be formed of both an n-type TFT and a p-type TFT or only either an n-type TFT or a p-type Furthermore, there is also no particular limitation on crystallinity of a semiconductor film used for the TFT. For example, an amorphous semiconductor film, a crystalline semiconductor film, an oxide semiconductor film, or the like can be used.

Note that the structure described in this embodiment can be combined as appropriate with any of the structures described in the other embodiments.

(Embodiment 3)

In this embodiment, as one embodiment of the present invention, a light-emitting element in which two or more kinds of organic compounds as well as a phosphorescent organometallic iridium complex are used for a light-emitting layer is described.

Figure 2A:
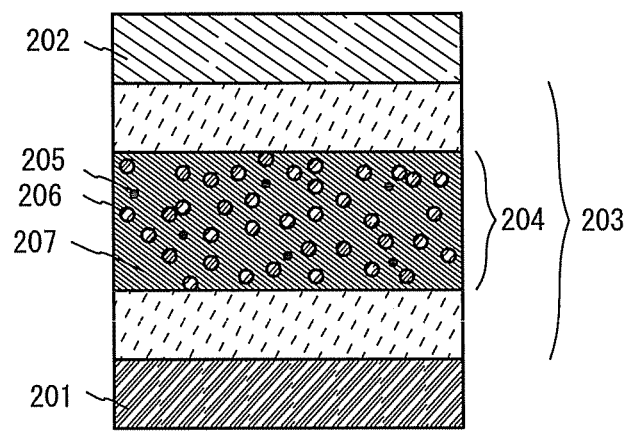
FIGS. 2A and 2B illustrate light-emitting elements of one embodiment of the present invention.
Figure 2B:
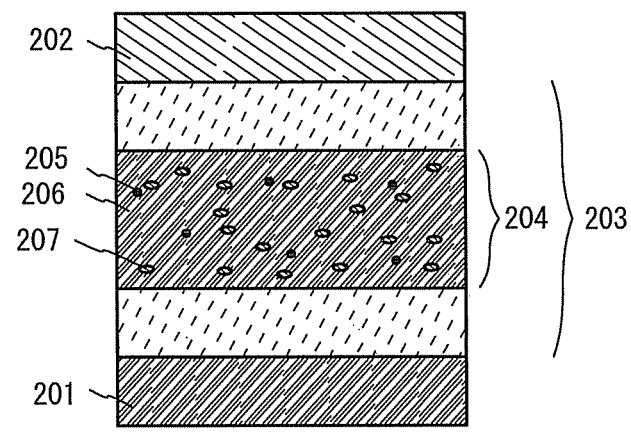

A light-emitting element described in this embodiment includes an EL layer 203 between a pair of electrodes (a first electrode 201 and a second electrode 202) as illustrated in FIG. 2A and FIG. 2B. Note that the EL layer 203 includes at least a light-emitting layer 204 and may include a hole-injection layer, a hole-transport layer, an electron-transport layer, an electron-injection layer, a charge-generation layer, and the like. Note that substances for the hole-injection layer, the hole-transport layer, the electron-transport layer, the electron-injection layer, and the charge-generation layer can be similar to the substances for the hole-injection layer 111, the hole-transport layer 112, the electron-transport layer 114, the electron-injection layer 115, and the charge-generation layer 116, respectively, which are described in Embodiment 2.

In this embodiment, the first electrode 201 functions as an anode, and the second electrode 202 functions as a cathode. Note that structures of the first electrode 201 and the second electrode 202 can be similar to those of the first electrode 101 and the second electrode 103 described in Embodiment 2.

The light-emitting layer 204 described in this embodiment contains a phosphorescent compound 205 using the organometallic complex described in Embodiment 1, a first organic compound 206 and a second organic compound 207. Note that the phosphorescent compound 205 is a guest material in the light-emitting layer 204. Moreover, one of the first organic compound 206 and the second organic compound 207, the content of which is higher than that of the other in the light-emitting layer 204, is a host material in the light-emitting layer 204. FIG. 2A represents a device where the second organic compound 207 is the host material while FIG. 2B represents a light-emitting element comprising a light-emitting layer in which the first organic compound 206 is the host material. Further, the light-emitting layer 204 may comprise other substances in addition to the phosphorescent compound 205, the first organic compound 206, and the second organic compound 207.

When the light-emitting layer 204 has the structure in which the guest material is dispersed in the host material, crystallization of the light-emitting layer can be suppressed. Further, it is possible to suppress concentration quenching due to high concentration of the guest material, and thus the light-emitting element can have higher emission efficiency.

It is preferable that a triplet excitation energy level ($T_1$ level) of each of the first organic compound 206 and the second organic compound 207 be higher than that of the phosphorescent compound 205. The reason for this is that when the $T_1$ level of the first organic compound 206 or the second organic compound 207 is lower than that of the phosphorescent compound 205, the triplet excitation energy of the phosphorescent compound 205, which contributes to light emission, is transferred to the first organic compound 206 or the second organic compound 207 and accordingly the emission efficiency decreases.

Here, it is preferable that an emission spectrum of a host material (a fluorescence spectrum or a phosphorescence spectrum) largely overlap with an absorption spectrum of a guest material (specifically, a spectrum in an absorption band on the longest wavelength (lowest energy) side).

However, in general, it is difficult to obtain an overlap between a fluorescence spectrum of a host material and an absorption spectrum in an absorption band on the longest wavelength (lowest energy) side of a guest material. The reason for this is that fluorescence is emitted from an energy level higher than that of phosphorescence, and the $T_1$ level of a host material whose fluorescence spectrum has a wavelength close to an absorption spectrum of a guest material on the longest wavelength side is lower than the $T_1$ level of the guest material.

Thus, in this embodiment, a combination of the first organic compound 206 and the second organic compound 207 preferably forms an exciplex (also referred to as excited complex). In that case, the first organic compound 206 and the second organic compound 207 form an exciplex by obtaining energy by recombination of electrons and holes at the time of recombination of carriers (electrons and holes) in the light-emitting layer 204. Fluorescence from the exciplex has a spectrum on a longer wavelength side than a fluorescence spectrum of the first organic compound 206 alone or the second organic compound 207 alone. Therefore, while the $T_1$ levels of the first organic compound and the second organic compound are kept higher than the $T_1$ level of the guest material, the fluorescence can overlap with the absorption band of the guest material on a longer wavelength side, which can maximize energy transfer from a singlet excited state.

For the phosphorescent compound 205, the phosphorescent organometallic iridium complex described in Embodiment 1 is used. The combination of the first organic compound 206 and the second organic compound 207 which forms an exciplex is preferably employed; a combination of a compound which is likely to accept electrons (a compound having an electron-trapping property) and a compound which is likely to accept holes (a compound having a hole-trapping property) is more preferably employed.

As examples of a compound which is likely to accept electrons, the following can be given: 2-[3-(dibenzothiophen-4-yl)phenyl]dibenzo[f,h]quinoxaline (abbreviation: 2mDBTPDBq-II), 2-[4-(3,6-diphenyl-9H-carbazol-9-yl) phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-II).

As examples of a compound which is likely to accept holes, the following can be given: 4-phenyl-4'-(9-phenyl-9H-carbazol-3-yl)triphenylamine (abbreviation: PCBA1BP), 3-[N-(1-naphthyl)-N-(9-phenylcarbazol-3-yl)amino]-9-phenylcarbazole (abbreviation: PCzPCN1), 4,4',4''-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenylcarbazol-3-yl)-N,N'-diphenylbenzene-1,3-diamine (abbreviation: PCA2B), N-(9,9-dimethyl-2-N',N'-diphenylamino-9H-fluoren-7-yl)diphenylamine (abbreviation: DPNF), N,N',N''-triphenyl-N,N',N''-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), 4,4'-bis[N-(3-methylphenyl)-N-phenylamino]biphenyl (abbreviation: TPD), 4,4'-bis[N-(4-diphenylaminophenyl)-N-phenylamino]biphenyl (abbreviation: DPAB), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), 3-[N-(9-phenylcarbazol-3-yl)-N-phenylamino]-9-phenylcarbazole (abbreviation: PCzPCA1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 4,4'-bis(N-{4-[N'-(3-methylphenyl)-N'-phenylamino]phenyl}-N-phenylamino)biphenyl (abbreviation: DNTPD), 3,6-bis[N-(4-diphenylaminophenyl)-N-(1-naphthyl)amino]-9-phenylcarbazole (abbreviation: PCzTPN2), and 3,6-bis[N-(9-phenylcarbazol-3-yl)-N-phenylamino]-9-phenylcarbazole (abbreviation: PCzPCA2).

As for the above-described first and second organic compounds 206 and 207, the present invention is not limited to the above examples. The combination is determined so that an exciplex can be formed, the emission spectrum of the exciplex overlaps with the absorption spectrum of the phosphorescent compound 205, and the peak of the emission spectrum of the exciplex has a longer wavelength than the peak of the absorption spectrum of the phosphorescent compound 205.

Note that in the case where a compound which is likely to accept electrons and a compound which is likely to accept holes are used for the first organic compound 206 and the second organic compound 207, carrier balance can be controlled by the mixture ratio of the compounds.

In the light-emitting element described in this embodiment, energy transfer efficiency can be improved owing to energy transfer utilizing an overlap between an emission spectrum of an exciplex and an absorption spectrum of a phosphorescent compound; accordingly, it is possible to achieve high external quantum efficiency of the light-emitting element.

Note that in another structure of the present invention, the light-emitting layer 204 can be formed using a host molecule having a hole-trapping property and a host molecule having an electron-trapping property as the two kinds of organic compounds other than the phosphorescent compound 205 that is the guest material so that a phenomenon (guest coupled with complementary hosts: GCCH) occurs in which holes and electrons are introduced to guest molecules existing in the two kinds of host molecules and the guest molecules are brought into an excited state.

At this time, the host molecule having a hole-trapping property and the host molecule having an electron-trapping property can be respectively selected from the above-described compounds which are likely to accept holes and the above-described compounds which are likely to accept electrons.

As a light-emitting device including the above light-emitting element, a passive matrix light-emitting device and an active matrix light-emitting device can be manufactured. It is also possible to manufacture a light-emitting device with a microcavity structure including the above light-emitting element, whose structure is changed as described in another embodiment. Each of the above light-emitting devices is included in the present invention.

Note that there is no particular limitation on the structure of the TFT in the case of manufacturing the active matrix light-emitting device. For example, a staggered TFT or an inverted staggered TFT can be used as appropriate. Further, a driver circuit formed over a TFT substrate may be formed of both an n-type TFT and a p-type TFT or only either an n-type TFT or a p-type TFT. Furthermore, there is also no particular limitation on crystallinity of a semiconductor film used for the TFT. For example, an amorphous semiconductor film, a crystalline semiconductor film, an oxide semiconductor film, or the like can be used.

Note that the structure described in this embodiment can be combined as appropriate with any of the structures described in the other embodiments.

(Embodiment 4)

In this embodiment, as one embodiment of the present invention, a light-emitting element (hereinafter referred to as tandem light-emitting element) in which a plurality of EL layers and a charge-generation layer interposed therebetween will be described.

Figure 3A:
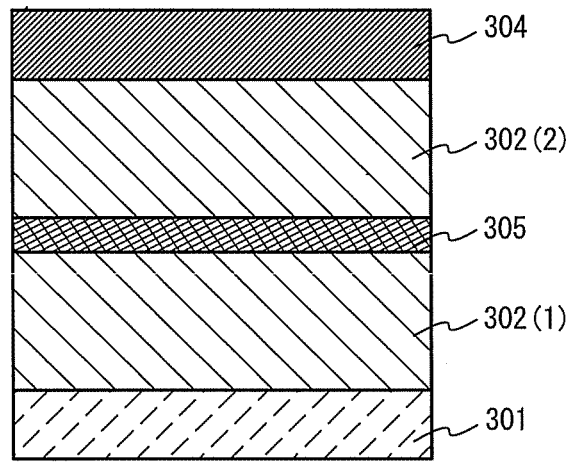
FIGS. 3A and 3B each illustrate a light-emitting element of one embodiment of the present invention.

A light-emitting element described in this embodiment is a tandem light-emitting element including a plurality of EL layers (a first EL layer 302(1) and a second EL layer 302(2)) between a pair of electrodes (a first electrode 301 and a second electrode 304) as illustrated in FIG. 3A.

In this embodiment, the first electrode 301 functions as an anode, and the second electrode 304 functions as a cathode. Note that the first electrode 301 and the second electrode 304 can have structures similar to those of the first electrode 101 and the second electrode 103 which are described in Embodiment 2.

In addition, although the plurality of EL layers (the first EL layer 302(1) and the second EL layer 302(2)) may have a structure similar to that of the EL layer described in Embodiment 2 or 3, any of the EL layers may have a structure similar to that of the EL layer described in Embodiment 2 or 3. In other words, the structures of the first EL layer 302(1) and the second EL layer 302(2) may be the same or different from each other and can be similar to those of the EL layers described in Embodiment 2 or 3.

Further, a charge-generation layer 305 is provided between the EL layers (the first EL layer 302(1) and the second EL layer 302(2)). The charge-generation layer 305 has a function of injecting electrons into one of the EL layers and injecting holes into the other of the EL layers when a voltage is applied between the first electrode 301 and the second electrode 304. For example, when a voltage is applied to the first electrode 301 such that the potential of the first electrode 301 is higher than that of the second electrode 304, the charge-generation layer 305 injects electrons into the first EL layer 302(1) and injects holes into the second EL layer 302(2).

Note that in terms of light extraction efficiency, the charge-generation layer 305 preferably has a light-transmitting property with respect to visible light (specifically, the charge-generation layer 305 has a visible light transmittance of 40% or more). Further, the charge-generation layer 305 functions even if it has lower conductivity than the first electrode 301 or the second electrode 304.

The charge-generation layer 305 may have either a structure (the composite material described in Embodiment 2) in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, for example, an aromatic amine compound such as NPB, TPD, TDATA, MTDATA, or 4,4'-bis[N-(spiro-9,9'-bifluoren-2-yl)-N-phenylamino]biphenyl (abbreviation: BSPB), or the like can be used. The substances mentioned here are mainly ones that have a hole mobility of $10^{-6}$ cm$^2$/Vs or higher. However, substances other than the above substances may be used as long as they are organic compounds having a hole-transport property higher than an electron-transport property.

Further, as the electron acceptor, 7,7,8,8-tetracyano-2,3,5,6-tetrafluoroquinodimethane (abbreviation: F$_4$-TCNQ), chloranil, or the like can be used. Alternatively, a transition metal oxide can be used. Further alternatively, an oxide of metals that belong to Group 4 to Group 8 of the periodic table can be used. Specifically, vanadium oxide, niobium oxide, tantalum oxide, chromium oxide, molybdenum oxide, tungsten oxide, manganese oxide, and rhenium oxide are preferable because their electron-accepting property is high. Among these, molybdenum oxide is especially preferable because it is stable in the air, has a low hygroscopic property, and is easily handled.

Note that the structure in which an electron acceptor is added to an organic compound having a high hole-transport property corresponds to the composite material described in Embodiment 2, and a structure similar to the composite material described in Embodiment 2 can be used; thus, the description is not repeated here. The description of the composite material in Embodiment 2 can be referred to.

On the other hand, in the case of the structure in which an electron donor is added to an organic compound having a high electron-transport property, as the organic compound having a high electron-transport property for example, a metal complex having a quinoline skeleton or a benzoquinoline skeleton, such as Alq, Almq$_3$, BeBq$_2$, or BAlq, or the like can be used. Alternatively, it is possible to use a metal complex having an oxazole-based ligand or a thiazole-based ligand, such as Zn(BOX)$_2$ or Zn(BTZ)$_2$. Further alternatively, instead of a metal complex, it is possible to use PBD, OXD-7, TAZ, BPhen, BCP, or the like. The substances mentioned here are mainly ones that have an electron mobility of $10^{-6}$ cm$^2$/Vs or higher. Note that substances other than the above substances may be used as long as they are organic compounds having an electron-transport property higher than a hole-transport property.

As the electron donor, it is possible to use an alkali metal, magnesium, an alkaline earth metal, a rare earth metal, a metal belonging to Group 13 of the periodic table, or an oxide or a carbonate thereof. Specifically, it is preferable to use lithium (Li), cesium (Cs), magnesium (Mg), calcium (Ca), ytterbium (Yb), indium (In), lithium oxide, cesium carbonate, or the like. Alternatively, an organic compound such as tetrathianaphthacene may be used as the electron donor.

Note that forming the charge-generation layer 305 by using any of the above materials can suppress an increase in drive voltage caused by the stack of the EL layers.

Figure 3B:
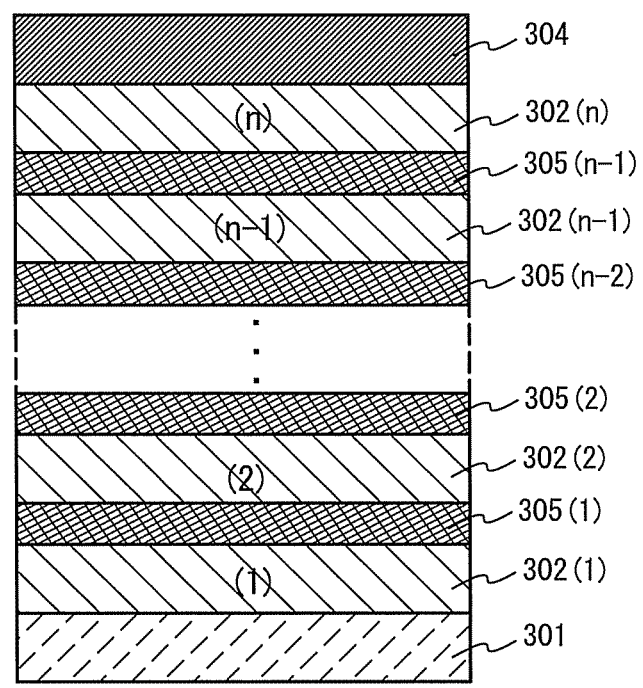

Although FIG. 3A illustrates the light-emitting element having two EL layers, the present invention can be similarly applied to a light-emitting element in which n EL layers (n is a natural number of three or more) are stacked as illustrated in FIG. 3B. In the case where a plurality of EL layers are included between a pair of electrodes as in the light-emitting element according to this embodiment, by provision of charge-generation layers between the EL layers, light emission in a high luminance region can be obtained with current density kept low. Since the current density can be kept low, the element can have a long lifetime. Moreover, it is possible to achieve a light-emitting device of low power consumption, which can be driven at a low voltage.

By making the EL layers emit light of different colors from each other, the light-emitting element can provide light emission of a desired color as a whole. For example, by forming a light-emitting element having two EL layers such that the emission color of the first EL layer and the emission color of the second EL layer are complementary colors, the light-emitting element can provide white light emission as a whole. Note that the word "complementary" means color relationship in which an achromatic color is obtained when colors are mixed. In other words, when lights obtained from substances which emit light of complementary colors are mixed, white emission can be obtained.

Further, the same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that the structure described in this embodiment can be combined as appropriate with any of the structures described in the other embodiments.

(Embodiment 5)

In this embodiment, as a light-emitting device utilizing phosphorescence which is one embodiment of the present invention, a light-emitting device using a phosphorescent organometallic iridium complex is described.

Figure 4:
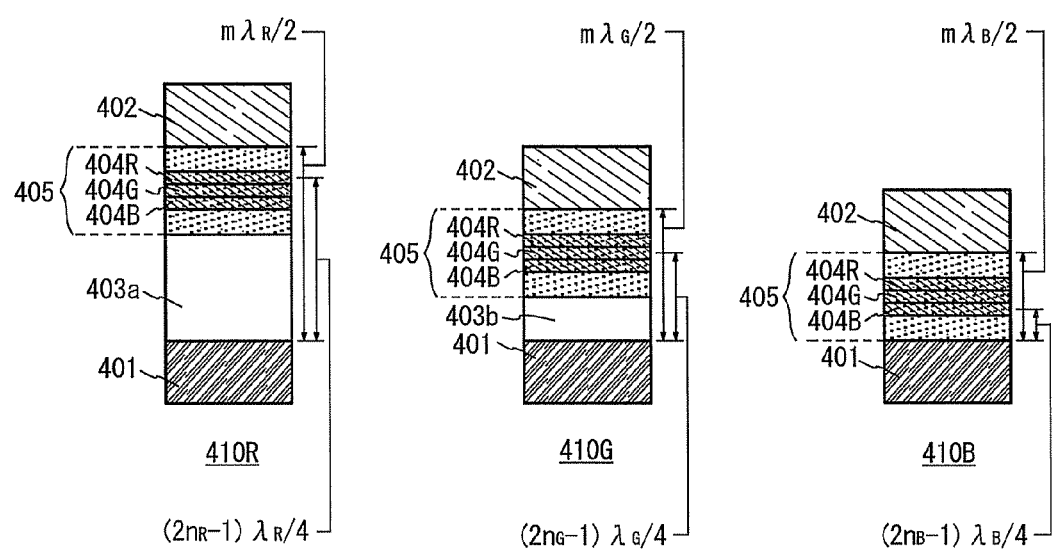
FIG. 4 illustrates light-emitting elements of one embodiment of the present invention.

A light-emitting device described in this embodiment has a micro optical resonator (microcavity) structure in which a light resonant effect between a pair of electrodes is utilized. The light-emitting device includes a plurality of light-emitting elements each of which has at least an EL layer 405 between a pair of electrodes (a reflective electrode 401 and a semi-transmissive and semi-reflective electrode 402) as illustrated in FIG. 4. Further, the EL layer 405 includes at least a light-emitting layer 404 serving as a light-emitting region and may further include a hole-injection layer, a hole-transport layer, an electron-transport layer, an electron-injection layer, a charge-generation layer, and the like. Note that the light-emitting layer 404 contains a phosphorescent organometallic iridium complex of one embodiment of the present invention.

In this embodiment, a light-emitting device is described which includes light-emitting elements (a first light-emitting element 410R, a second light-emitting element 410G, and a third light-emitting element 410B) having different structures as illustrated in FIG. 4.

The first light-emitting element 410R has a structure in which a first transparent conductive layer 403a, an EL layer 405, and a semi-transmissive and semi-reflective electrode 402 are sequentially stacked over a reflective electrode 401. The second light-emitting element 410G has a structure in which a second transparent conductive layer 403b, the EL layer 405, and the semi-transmissive and semi-reflective electrode 402 are sequentially stacked over the reflective electrode 401. The third light-emitting element 410B has a structure in which the EL layer 405 and the semi-transmissive and semi-reflective electrode 402 are sequentially stacked over the reflective electrode 401.

Note that the reflective electrode 401, the EL layer 405, and the semi-transmissive and semi-reflective electrode 402 are common to the light-emitting elements (the first light-emitting element 410R, the second light-emitting element 410G, and the third light-emitting element 410B).

Further, the EL layer 405 includes a first light-emitting layer 404B, a second light-emitting layer 404G, and a third light-emitting layer 404R. Note that the first light-emitting layer 404B emits light having a peak at a wavelength of $\lambda_B$. The second light-emitting layer 404G emits light having a peak at a wavelength of $\lambda_G$. The third light-emitting layer 404R emits light having a peak at a wavelength of $\lambda_R$. Thus, from each of the light-emitting elements (the first light-emitting element 410R, the second light-emitting element 410G, and the third light-emitting element 410B), light emitted from the first light-emitting layer 404B, light emitted from the second light-emitting layer 404G, and light emitted from the third light-emitting layer 404R which overlap with each other can be obtained. Note that the above wavelengths satisfy the relation of $\lambda_B < \lambda_G < \lambda_R$.

Each of the light-emitting elements described in this embodiment has a structure in which the EL layer 405 is interposed between the reflective electrode 401 and the semi-transmissive and semi-reflective electrode 402. Light emitted in all directions from the light-emitting layers included in the EL layer 405 is resonated by the reflective electrode 401 and the semi-transmissive and semi-reflective electrode 402 which function as a micro optical resonator (microcavity). Note that the reflective electrode 401 is formed using a conductive material having reflectivity, and a film whose visible light reflectivity is 40% to 100%, preferably 70% to 100%, and whose resistivity is $1 \times 10^{-2}$ Ωcm or lower is used. In addition, the semi-transmissive and semi-reflective electrode 402 is formed using a conductive material having reflectivity and a light-transmitting property, and a film whose visible light reflectivity is 20% to 80%, preferably 40% to 70%, and whose resistivity is $1 \times 10^{-2}$ Ωcm or lower is used.

In this embodiment, the thicknesses of the transparent conductive layers (the first transparent conductive layer 403a and the second transparent conductive layer 403b) provided in the first light-emitting element 410R and the second light-emitting element 410G, respectively, are varied between the light-emitting elements, whereby the light-emitting elements differ in the optical path length from the reflective electrode 401 to the semi-transmissive and semi-reflective electrode 402. In other words in the case of light emitted from the light-emitting layers of each of the light-emitting elements, thus having a broad emission spectrum, light with a wavelength that is resonated between the reflective electrode 401 and the semi-transmissive and semi-reflective electrode 402 can be enhanced while light with a wavelength that is not resonated therebetween can be attenuated. Thus, when the elements differ in the optical path length from the reflective electrode 401 to the semi-transmissive and semi-reflective electrode 402, light with different wavelengths can be enhanced to be extracted.

Note that the optical path length (also referred to as optical distance) is expressed as a product of an actual distance and a refractive index, and in this embodiment, is a product of an actual thickness and n (refractive index). That is, an optical path length=actual thickness×n.

Note that the optical path length from the reflective electrode 401 to the semi-transmissive and semi-reflective electrode 402 is set to $m\lambda_R/2$ (m is a natural number of 1 or more) in the first light-emitting element 410R; the optical path length from the reflective electrode 401 to the semi-transmissive and semi-reflective electrode 402 is set to $m\lambda_G/2$ (m is a natural number of 1 or more) in the second light-emitting element 410G; and the optical path length from the reflective electrode 401 to the semi-transmissive and semi-reflective electrode 402 is set to $m\lambda_B/2$ (m is a natural number of 1 or more) in the third light-emitting element 410B.

In this manner, the light ($\lambda_R$) emitted from the third light-emitting layer 404R included in the EL layer 405 is mainly enhanced to be extracted from the first light-emitting element 410R, the light ($\lambda_G$) emitted from the second light-emitting layer 404G included in the EL layer 405 is mainly enhanced to be extracted from the second light-emitting element 410E and the light ($\lambda_B$) emitted from the first light-emitting layer 404B included in the EL layer 405 is mainly enhanced to be extracted from the third light-emitting element 410B. Note that the light extracted from each of the light-emitting elements is emitted from the semi-transmissive and semi-reflective electrode 402 side.

Note that in the above structure, strictly speaking, the optical path length from the reflective electrode 401 to the semi-transmissive and semi-reflective electrode 402 can be the length from a reflection region in the reflective electrode 401 to a reflection region in the semi-transmissive and semi-reflective electrode 402. However, it is difficult to precisely determine the positions of the reflection regions in the reflective electrode 401 and the semi-transmissive and semi-reflective electrode 402; therefore, it is assumed that the above effect can be sufficiently obtained wherever the reflection regions may be set in the reflective electrode 401 and the semi-transmissive and semi-reflective electrode 402.

Further, the optical path length from the reflective electrode 401 to the third light-emitting layer 404R is preferably adjusted to $(2n_R-1)\lambda_R/4$, where $n_R$ is a natural number of 1 or more, because in the first light-emitting element 410R, light (first reflected light) that is reflected by the reflective electrode 401 of the light emitted from the third light-emitting layer 404R considerably interferes with light (first incident light) that directly enters the semi-transmissive and semi-reflective electrode 402 from the third light-emitting layer 404R. By adjusting the optical path length, the phases of the first reflected light and the first incident light can be aligned with each other and the light emitted from the third light-emitting layer 404R can be further amplified.

Note that strictly speaking, the optical path length from the reflective electrode 401 to the third light-emitting layer 404R can be the optical path length from a reflection region in the reflective electrode 401 to a light-emitting region in the third light-emitting layer 404R. However, it is difficult to precisely determine the positions of the reflection region in the reflective electrode 401 and the light-emitting region in the third light-emitting layer 404R; therefore, it is assumed that the above effect can be sufficiently obtained wherever the reflection region and the light-emitting region may be set in the reflective electrode 401 and the third light-emitting layer 404R, respectively.

Next, the optical path length of the second light-emitting element 410G which emits light with the wavelength of $\lambda_G$ and that of the light-emitting element 410B which emits light with the wavelength of $\lambda_B$ are adjusted in a similar manner to the optical path length of light-emitting element 410R, whereby light emitted from each of the light-emitting elements can be amplified.

Note that although each of the light-emitting elements in the above-described structure includes a plurality of light-emitting layers in the EL layer, the present invention is not limited thereto; for example, the structure of the tandem light-emitting element which is described in Embodiment 4 can be combined, in which case a plurality of EL layers are provided so that a charge-generation layer is interposed therebetween in one light-emitting element and one or more light-emitting layers are formed in each of the EL layers.

The light-emitting device described in this embodiment has a microcavity structure, in which light with wavelengths which differ depending on the light-emitting elements can be extracted even when they include the same EL layers, so that it is not needed to form light-emitting elements for the colors of R, G, and B. Therefore, the above structure is advantageous for full color display owing to easiness in achieving higher resolution display or the like. Further, with the use of color filters at the same time, light with higher purity can be obtained and the light-emitting device can have high color reproductivity. In addition, emission intensity with a predetermined wavelength in the front direction can be increased, whereby power consumption can be reduced. The above structure is particularly useful in the case of being applied to a color display (image display device) including pixels of three or more colors but may also be applied to lighting or the like.

(Embodiment 6)

In this embodiment, a light-emitting device including a light-emitting element in which an organometallic complex that is one embodiment of the present invention is used for a light-emitting layer is described.

The light-emitting device can be either a passive matrix light-emitting device or an active matrix light-emitting device. Note that any of the light-emitting elements described in the other embodiments can be applied to the light-emitting device described in this embodiment.

In this embodiment, an active matrix light-emitting device is described with reference to FIGS. 5A and 5B.

Figure 5A:
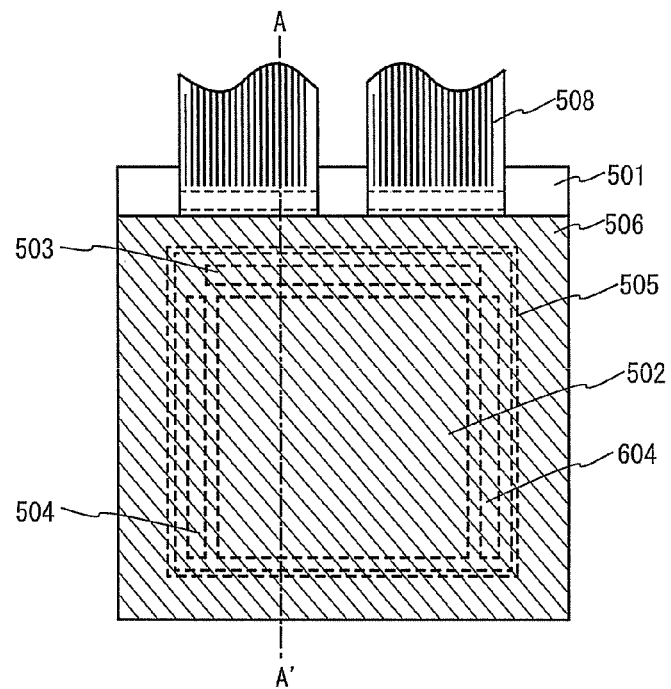
FIGS. 5A and 5B illustrate an active matrix light-emitting device.
Figure 5B:
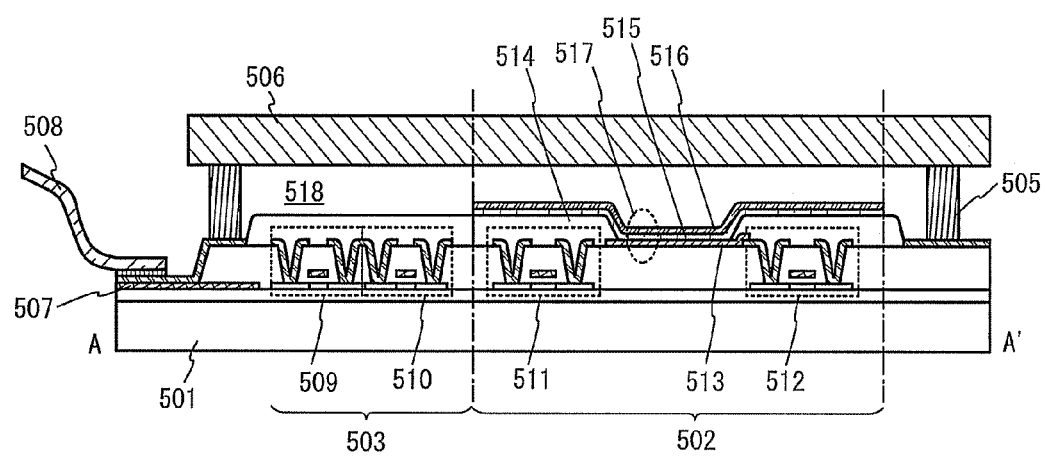

Note that FIG. 5A is a top view illustrating a light-emitting device and FIG. 5B is a cross-sectional view taken along the chain line A-A' in FIG. 5A. The active matrix light-emitting device according to this embodiment includes a pixel portion 502 provided over an element substrate 501, a driver circuit portion (a source line driver circuit) 503, and a driver circuit portion (a gate line driver circuit) 504. The pixel portion 502, the driver circuit portion 503, and the driver circuit portion 504 are sealed between the element substrate 501 and a sealing substrate 506 by a sealant 505.

In addition, a lead wiring 507 is provided over the element substrate 501. The lead wiring 507 is provided for connecting an external input terminal through which a signal (e.g., a video signal, a clock signal, a start signal, and a reset signal) or a potential from the outside is transmitted to the driver circuit portion 503 and the driver circuit portion 504. Here is shown an example in which a flexible printed circuit (FPC) 508 is provided as the external input terminal. Although the FPC 508 is illustrated alone, this FPC may be provided with a printed wiring board (PWB). The light-emitting device in the present specification includes, in its category, not only the light-emitting device itself but also the light-emitting device provided with the FPC or the PWB.

Next, a cross-sectional structure is described with reference to FIG. 5B. The driver circuit portion and the pixel portion are formed over the element substrate 501; here are illustrated the driver circuit portion 503 which is the source line driver circuit and the pixel portion 502.

The driver circuit portion 503 is an example where a CMOS circuit is formed, which is a combination of an n-channel TFT 509 and a p-channel TFT 510. Note that a circuit included in the driver circuit portion may be formed using various CMOS circuits, PMOS circuits, or NMOS circuits. Although this embodiment shows a driver integrated type in which the driver circuit is formed over the substrate, the driver circuit is not necessarily formed over the substrate, and the driver circuit can be formed outside, not over the substrate.

The pixel portion 502 is formed of a plurality of pixels each of which includes a switching TFT 511, a current control TFT 512, and a first electrode 513 which is electrically connected to a wiring (a source electrode or a drain electrode) of the current control TFT 512. Note that an insulator 514 is formed to cover end portions of the first electrode 513. In this embodiment, the insulator 514 is formed using a positive photosensitive acrylic resin.

The insulator 514 preferably has a curved surface with curvature at an upper end portion or a lower end portion thereof in order to obtain favorable coverage by a film which is to be stacked over the insulator 514. For example, in the case of using a positive photosensitive acrylic resin as a material for the insulator 514, the insulator 514 preferably has a curved surface with a radius of curvature (0.2 µm to 3 µm) at the upper end portion. Note that the insulator 514 can be formed using either a negative photosensitive resin or a positive photosensitive resin. It is possible to use, without limitation to an organic compound, either an organic compound or an inorganic compound such as silicon oxide or silicon oxynitride.

An EL layer 515 and a second electrode 516 are stacked over the first electrode 513. In the EL layer 515, at least a light-emitting layer is provided which contains an organometallic complex that is one embodiment of the present invention. Further, in the EL layer 515, a hole-injection layer, a hole-transport layer, an electron-transport layer, an electron-injection layer, a charge-generation layer, and the like can be provided as appropriate in addition to the light-emitting layer.

A light-emitting element 517 is foamed of a stacked structure of the first electrode 513, the EL layer 515, and the second electrode 516. For the first electrode 513, the EL layer 515, and the second electrode 516, the materials described in Embodiment 2 can be used. Although not illustrated, the second electrode 516 is electrically connected to an FPC 508 which is an external input terminal.

Note that in this embodiment, the first electrode 513 functions as an anode, and the second electrode 516 functions as a cathode.

Although the cross-sectional view of FIG. 5B illustrates only one light-emitting element 517, a plurality of light-emitting elements are arranged in matrix in the pixel portion 502. Light-emitting elements which provide three kinds of light emission (R, G, and B) are selectively formed in the pixel portion 502, whereby a light-emitting device capable of full color display can be fabricated. Alternatively, a light-emitting device which is capable of full color display may be fabricated by a combination with color filters.

Further, the sealing substrate 506 is attached to the element substrate 501 with the sealant 505, whereby a light-emitting element 517 is provided in a space 518 surrounded by the element substrate 501, the sealing substrate 506, and the sealant 505. The space 518 may be filled with an inert gas (such as nitrogen or argon), or the sealant 505.

An epoxy-based resin is preferably used for the sealant 505. It is preferable that such a material do not transmit moisture or oxygen as much as possible. As the sealing substrate 506, a glass substrate, a quartz substrate, or a plastic substrate formed of fiberglass reinforced plastic (FRP), polyvinyl fluoride (PVF), polyester, acrylic, or the like can be used.

As described above, an active matrix light-emitting device can be obtained.

Note that the structure described in this embodiment can be combined as appropriate with any of the structures described in the other embodiments.

(Embodiment 7)

In this embodiment, examples of a variety of electronic devices which are completed using a light-emitting device will be described with reference to FIGS. 6A to 6D. To the light-emitting device, an organometallic complex that is one embodiment of the present invention is applied.

Examples of the electronic devices to which the light-emitting device is applied are a television device (also referred to as television or television receiver), a monitor of a computer or the like, a camera such as a digital camera or a digital video camera, a digital photo frame, a mobile phone (also referred to as cellular phone or cellular phone device), a portable game machine, a portable information terminal, an audio reproducing device, and a large-sized game machine such as a pachinko machine. Specific examples of these electronic devices are illustrated in FIGS. 6A to 6D.

Figure 6A:
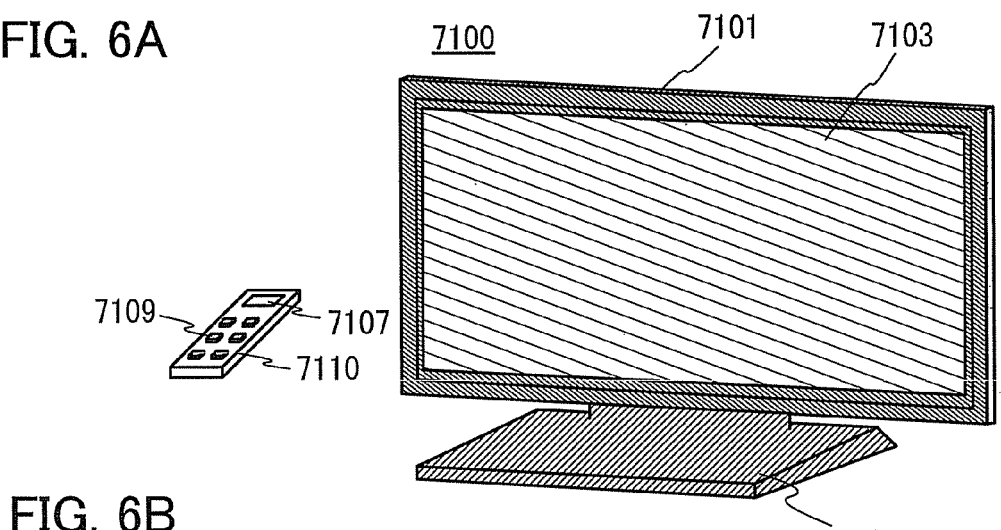
FIGS. 6A to 6D illustrate electronic devices.

FIG. 6A illustrates an example of a television set. In a television set 7100, a display portion 7103 is incorporated in a housing 7101. Images can be displayed on the display portion 7103, and the light-emitting device can be used for the display portion 7103. In addition, here, the housing 7101 is supported by a stand 7105.

Operation of the television set 7100 can be performed with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television set 7100 is provided with a receiver, a modem, and the like. With the receiver, a general television broadcast can be received. Furthermore, when the television set 7100 is connected to a communication network by wired or wireless connection via the modem, one-way (from a transmitter to a receiver) or two-way (between a transmitter and a receiver, between receivers, or the like) data communication can be performed.

Figure 6B:
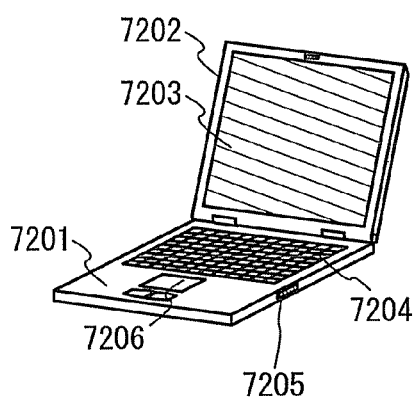

FIG. 6B illustrates a computer having a main body 7201, a housing 7202, a display portion 7203, a keyboard 7204, an external connection port 7205, a pointing device 7206, and the like. Note that this computer is manufactured using the light-emitting device for the display portion 7203.

Figure 6C:
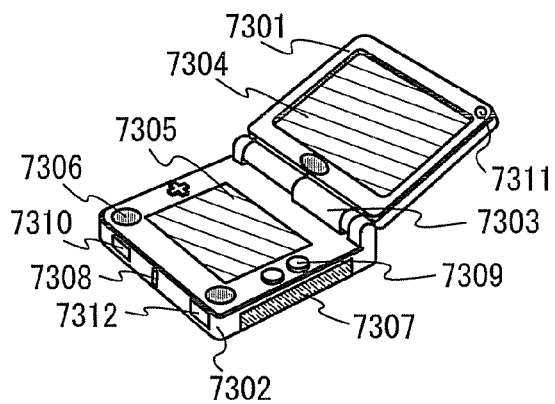

FIG. 6C illustrates a portable game machine having two housings, a housing 7301 and a housing 7302, which are connected with a joint portion 7303 so that the portable game machine can be opened or folded. A display portion 7304 is incorporated in the housing 7301, and a display portion 7305 is incorporated in the housing 7302. In addition, the portable game machine illustrated in FIG. 6C includes a speaker portion 7306, a recording medium insertion portion 7307, an LED lamp 7308, an input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), and a microphone 7312), and the like. Needless to say, the structure of the portable game machine is not limited to the above as long as the light-emitting device is used for at least one of the display portion 7304 and the display portion 7305, and may include other accessories as appropriate. The portable game machine illustrated in FIG. 6C has a function of reading out a program or data stored in a storage medium to display it on the display portion, and a function of sharing information with another portable game machine by wireless communication. The portable game machine illustrated in FIG. 6C can have a variety of functions without limitation to the above.

Figure 6D:
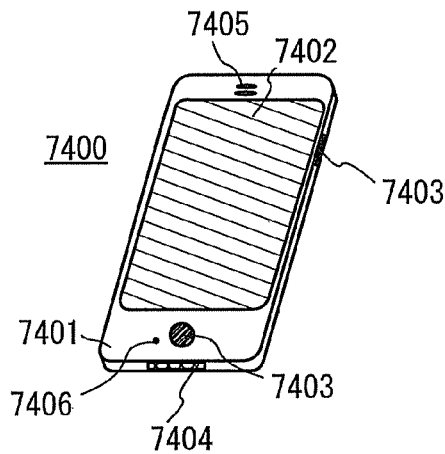

FIG. 6D illustrates an example of a mobile phone. A mobile phone 7400 is provided with a display portion 7402 incorporated in a housing 7401, operation buttons 7403, an external connection port 7404, a speaker 7405, a microphone 7406, and the like. Note that the mobile phone 7400 is manufactured using the light-emitting device for the display portion 7402.

When the display portion 7402 of the mobile phone 7400 illustrated in FIG. 6D is touched with a finger or the like, data can be input to the mobile phone 7400. Further, operations such as making a call and composing an e-mail can be performed by touching the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or composing an e-mail, a text input mode mainly for inputting text is selected for the display portion 7402 so that text displayed on the screen can be input. In this case, it is preferable to display a keyboard or number buttons on almost the entire screen of the display portion 7402.

When a detection device including a sensor for detecting inclination, such as a gyroscope or an acceleration sensor, is provided inside the mobile phone 7400, display on the screen of the display portion 7402 can be automatically switched by determining the orientation of the mobile phone 7400 (whether the mobile phone is placed horizontally or vertically for a landscape mode or a portrait mode).

The screen modes are switched by touching the display portion 7402 or operating the operation buttons 7403 of the housing 7401. The screen modes can also be switched depending on the kind of image displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed for a certain period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken when the display portion 7402 is touched with the palm or the finger, whereby personal authentication can be performed. Further, by providing a backlight or a sensing light source which emits near-infrared light in the display portion, an image of a finger vein, a palm vein, or the like can be taken.

As described above, the electronic devices can be obtained by application of the light-emitting device according to one embodiment of the present invention. The light-emitting device has a remarkably wide application range, and can be applied to electronic devices in a variety of fields.

Note that the structure described in this embodiment can be combined as appropriate with any of the structures described in the other embodiments.

(Embodiment 8)

In this embodiment, examples of a lighting device to which a light-emitting device including an organometallic complex that is one embodiment of the present invention is applied will be described with reference to FIG. 7.

Figure 7:
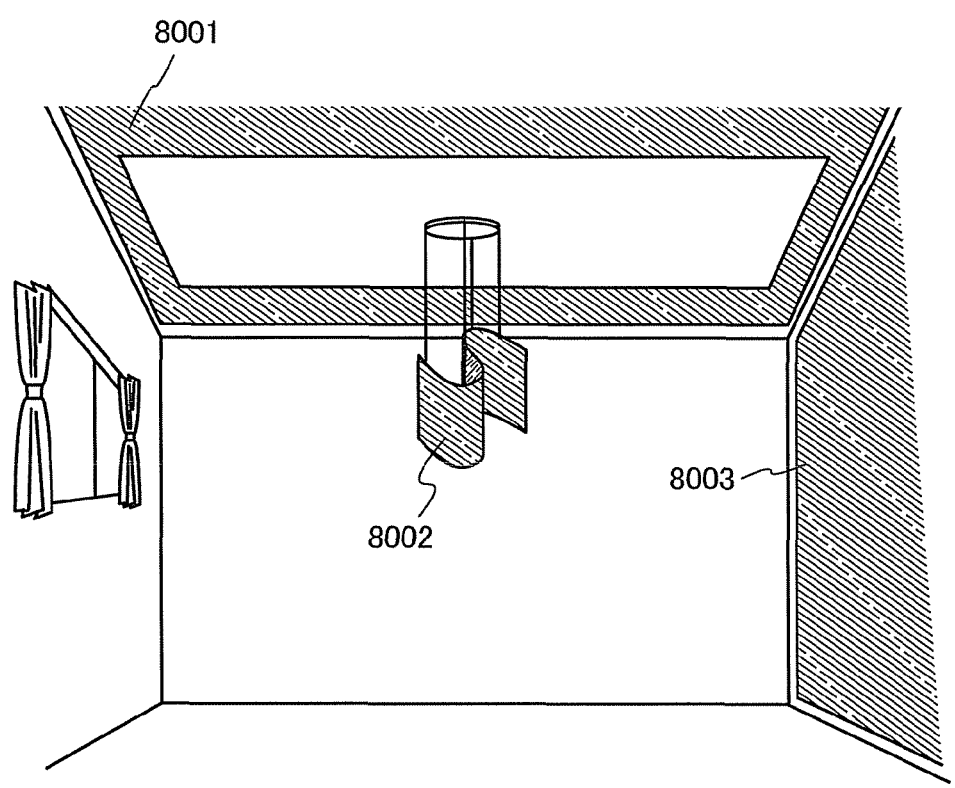
FIG. 7 illustrates lighting devices.

FIG. 7 illustrates an example in which the light-emitting device is used as an indoor lighting device 8001. Since the light-emitting device can have a large area, it can be used for a lighting device having a large area. In addition, a lighting device 8002 in which a light-emitting region has a curved surface can also be obtained with the use of a housing with a curved surface. A light-emitting element included in the light-emitting device described in this embodiment is in a thin film form, which allows the housing to be designed more freely. Therefore, the lighting device can be elaborately designed in a variety of ways. Further, a wall of the room may be provided with a large-sized lighting device 8003.

In this manner, a variety of lighting devices to which the light-emitting device is applied can be obtained. Note that such lighting devices are also embodiments of the present invention.

Note that the structure described in this embodiment can be combined as appropriate with any of the structures described in the other embodiments.

(Embodiment 9)

Figure 8:
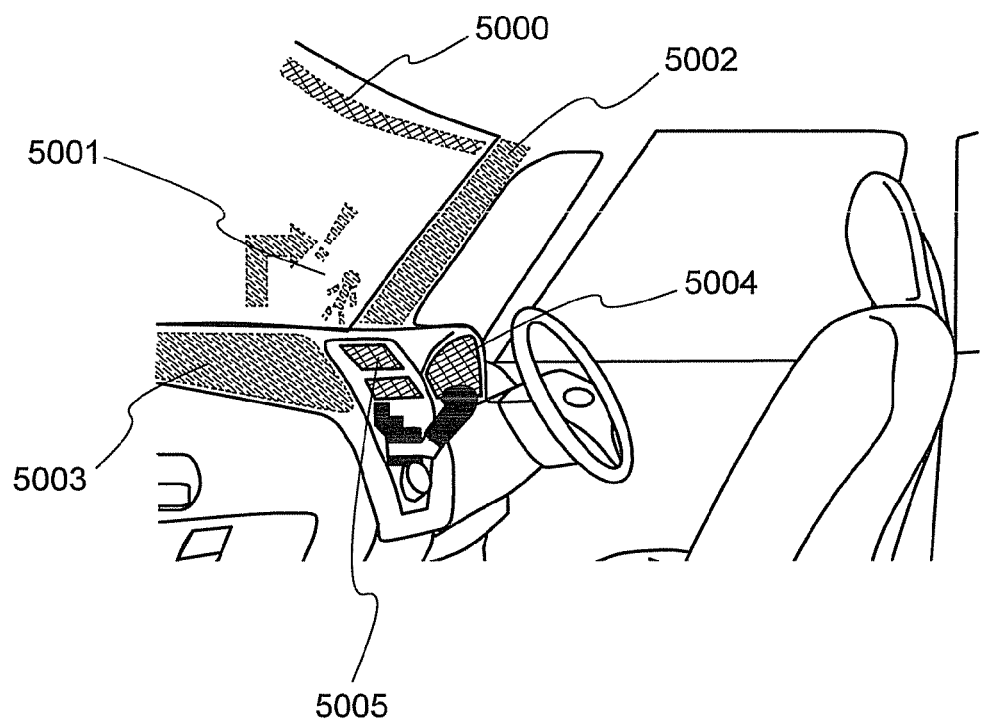
FIG. 8 illustrates examples of vehicle-mounted display devices according to one embodiment of the present invention.

The light-emitting element including the organometallic complex of one embodiment of the present invention can also be used in an automobile windshield or an automobile dashboard. FIG. 8 illustrates one mode in which the light-emitting element including the organometallic complex of one embodiment of the present invention is used for an automobile windshield and an automobile dashboard. In regions 5000 to 5005, display is performed with the use of the light-emitting element including the organometallic complex of one embodiment of the present invention.

Light-emitting devices which incorporate the light-emitting element including the organometallic complex of one embodiment of the present invention are provided in the regions 5000 and 5001 in the automobile windshield. The light-emitting element including the organometallic complex of one embodiment of the present invention can be formed into what is called a see-through light-emitting device, through which the opposite side can be seen, by including a first electrode and a second electrode formed with electrodes having a light-transmitting property. Such see-through light-emitting devices can be provided even in the automobile windshield without hindering the vision. Further, for example, in the case where a transistor for driving the light-emitting element is provided, it is preferable to use a transistor having a light-transmitting property, such as an organic transistor using an organic semiconductor material or a transistor using an oxide semiconductor.

A light-emitting device which incorporates the light-emitting element including the organometallic complex of one embodiment of the present invention is provided in the region 5002 in a pillar portion. An image taken by an imaging unit provided in the car body is shown in the region 5002, whereby the view hindered by the pillar portion can be compensated for. Similarly, the view hindered, by the car body can be compensated for by showing an image taken by an imaging unit provided in the outside of the car body, in the region 5003 provided in the dashboard; thus, elimination of blind areas and enhancement of safety can be achieved. Showing an image so as to compensate for the area which a driver cannot see, makes it possible for the driver to confirm safety easily and comfortably.

A variety of kinds of information such as information of navigation, speedometer, tachometer, mileage, fuel meter, gearshift indicator, and air condition can be shown in the regions 5004 and 5005. The contents or layout of the display can be changed by a user as appropriate. Further, such information can be shown in the regions 5000 to 5003. Note that the regions 5000 to 5005 can also be used as lighting.

The light-emitting element including the organometallic complex of one embodiment of the present invention can have high emission efficiency and low power consumption. Moreover, the light-emitting element can be fabricated inexpensively. Therefore, even when a large number of large screens are provided as in the regions 5000 to 5005, load on a battery can be reduced, which provides comfortable use. Thus, the light-emitting device using the light-emitting element including the organometallic complex of one embodiment of the present invention can be suitably used as an in-vehicle light-emitting device. Further, the light-emitting device can be mounted inexpensively.

EXAMPLE 1

SYNTHESIS EXAMPLE 1

In this example, a synthesis example of tris(3-phenyl-5,6,7,8-tetrahydro-4H-1,2,4-triazolo[4,3-a]pyridinato)iridium (III) (abbreviation: [Ir(ptzpytH)$_3$]), the organometallic complex described in Embodiment 1, is specifically described. A structural formula of [Ir(ptzpytH)$_3$] is shown below.

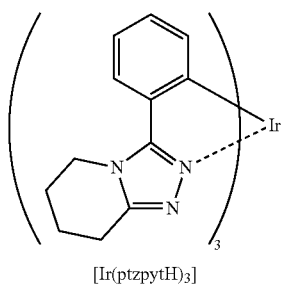

(100)

[Ir(ptzpytH)$_3$]

Step 1: Synthesis of 3-Phenyl-5,6,7,8-tetrahydro-4H-1,2,4-triazolo[4,3-a]pyridine (Abbreviation: HptzpytH)

In a 300-mL three-neck flask were put 6.0 g of benzoylhydrazine and 100 mL of xylene. To this mixture was added 5.0 g of O-methyl valerolactam and the mixture was heated and refluxed at 140° C. for 3 hours in a nitrogen stream. After the reflux, the reaction solution was concentrated to give a solid. A small amount of ethyl acetate was added to the obtained solid and suction filtration was performed to obtain 3-phenyl-5,6,7,8-tetrahydro-4H-1,2,4-triazolo[4,3-a]pyridine (abbreviation: HptzpytH) as a white solid in 77% yield. The synthetic scheme of Step 1 is shown in (a-1).

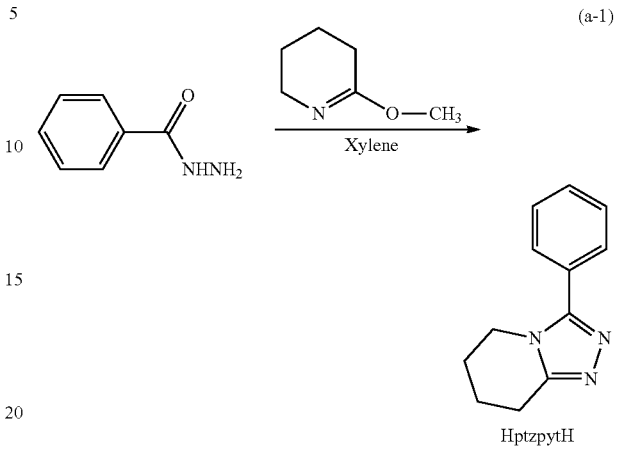

Step 2: Synthesis of Tris(3-phenyl-5,6,7,8-tetrahydro-4H-1,2,4-triazolo[4,3-a]pyridinato)iridium(III) (Abbreviation: [Ir(ptzpytH)$_3$])

In a reaction container provided with a three-way cock were put 7.3 g of the ligand HptzpytH that was prepared in Step 1 and 0.71 g of tris(acetylacetonato)iridium(III), and the air in the reaction container was replaced with argon. Then, the mixture was heated at 250° C. for 48 hours to be reacted. The obtained reaction mixture was dissolved in dichloromethane and purification by alumina column chromatography was performed. Dichloromethane was used as a developing solvent. The obtained fraction was concentrated to obtain a solid. The obtained solid was recrystallized with a mixed solvent of dichloromethane and ethyl acetate to obtain the organometallic complex [Ir(ptzpytH)$_3$] (yellow powder, 30% yield). The synthetic scheme of Step 2 is shown in (b-1).

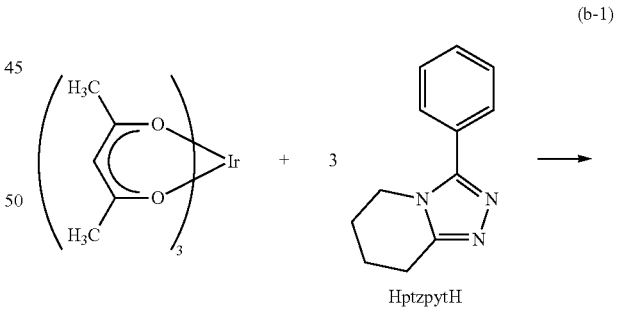

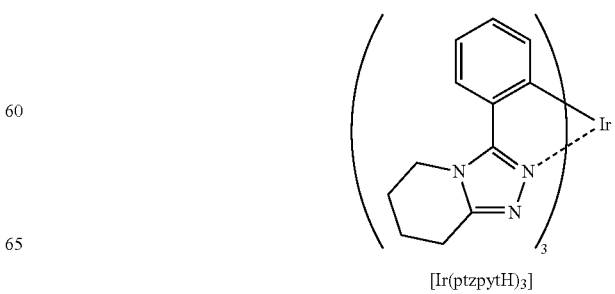

[Ir(ptzpytH)$_3$]

Figure 9:
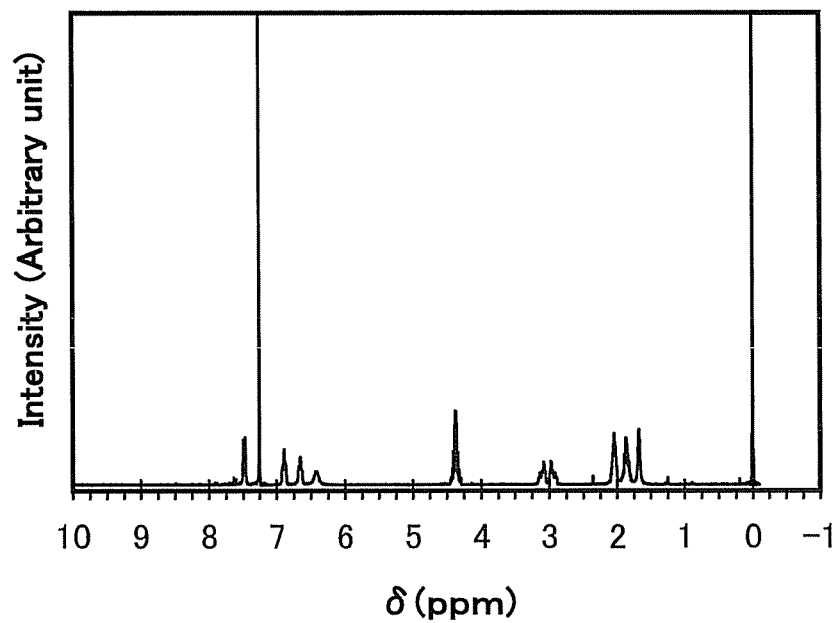
FIG. 9 is a $^1$H NMR chart of [Ir(ptzpytH)$_3$], an organometallic complex represented by Structural Formula (100).

An analysis result by nuclear magnetic resonance spectroscopy ($^1$H-NMR) of the yellow powder prepared in Step 2 described above is shown below. The $^1$H NMR chart is shown in FIG. 9. These results revealed that [Ir(ptzpytH)$_3$], the organometallic complex of one embodiment of the present invention which is represented by Structural Formula (100), was obtained in Synthesis Example 1.

$^1$H NMR data of the obtained substance are as follows:

$^1$H-NMR. δ (CDCl$_3$): 1.81-1.91 (m, 2H), 2.04 (br, 2H), 2.92-3.13 (m, 2H), 4.30-4.44 (m, 2H), 6.42 (br, 1H), 6.66 (t, 1H), 6.89 (t, 1H), 7.48 (d, 1H)

Figure 10:
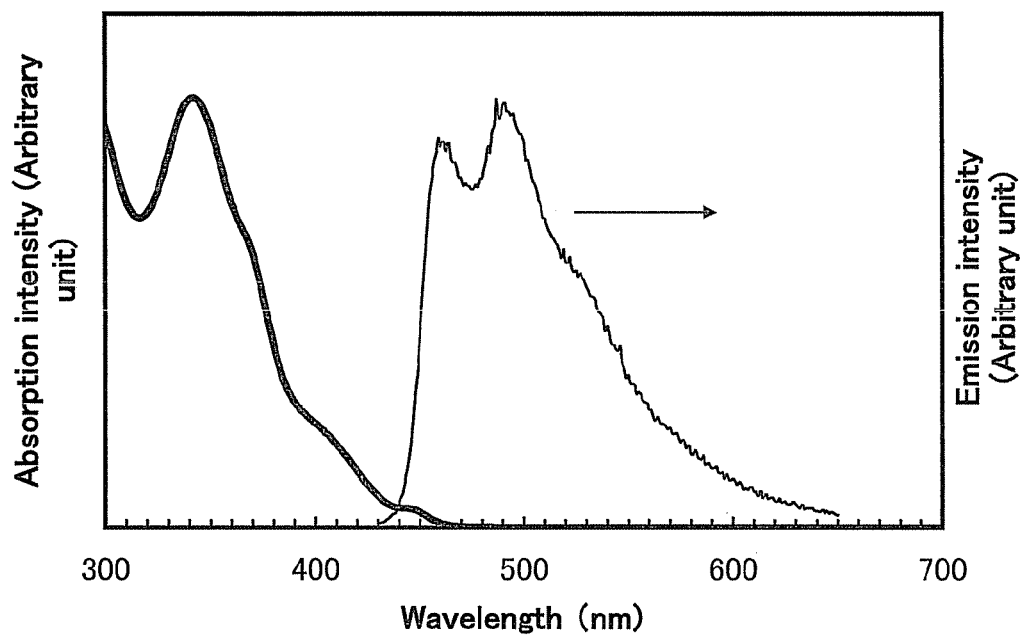
FIG. 10 shows an ultraviolet-visible absorption spectrum and an emission spectrum of [Ir(ptzpytH)$_3$], an organometallic complex represented by Structural Formula (100), in a dichloromethane solution.

Next, an ultraviolet-visible absorption spectrum (hereinafter, simply referred to as absorption spectrum) and an emission spectrum of [Ir(ptzpytH)$_3$] in a dichloromethane solution were measured. The absorption spectrum was measured with the use of an ultraviolet-visible light spectrophotometer (V-550, manufactured by JASCO Corporation) in the state where the dichloromethane solution (0.102 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (0.102 mmol/L) was put in a quartz cell at room temperature. FIG. 10 shows measurement results of the absorption spectrum and the emission spectrum. The horizontal axis represents wavelength and the vertical axes represent absorption intensity and emission intensity. Note that the absorption spectrum in FIG. 10 is a result obtained by subtraction of a measured absorption spectrum of only dichloromethane that was put in a quartz cell from the measured absorption spectrum of the dichloromethane solution of [Ir(ptzpytH)$_3$] in a quartz cell.

As shown in FIG. 10, [Ir(ptzpytH)$_3$], the organometallic complex of one embodiment of the present invention, has emission peaks at 459 nm and 487 nm, and blue light was observed from the dichloromethane solution.

As described above, [Ir(ptzpytH)$_3$] synthesized in this example, the organometallic complex described in Embodiment 1, is a light-emitting substance which emits blue phosphorescence. The number of synthesis steps as small as two and the favorable yield show that [Ir(ptzpytH)$_3$] is an organometallic complex which can be manufactured inexpensively. Note that the yield of tris (4,5-dimethyl-3-phenyl-4H-1,2,4-triazolato)iridium(III) (abbreviation: [Ir(Mptz-Me)$_3$]), a substance in which not an alicyclic ring but methyl groups are bonded to the 4-position and the 5-position of the ligand of [Ir(ptzpytH)$_3$], was rather poor. [Ir(ptzpytH)$_3$], the organometallic complex in which the ligand is a 3-aryl-5,6,7,8-tetrahydro-4H-[1,2,4]triazolo[4,3-a]pyridine derivative as in this example, can be synthesized with a high yield as described above, and the number of synthesis steps is small; thus, [Ir(ptzpytH)$_3$] is a blue phosphorescent material which can be very inexpensively synthesized.

EXAMPLE 2

In this example, a light-emitting element was fabricated which includes tris(3-phenyl-5,6,7,8-tetrahydro-4H-1,2,4-triazolo[4,3-a]pyridinato)iridium(III) (abbreviation: [Ir(ptzpytH)$_3$]), the organometallic complex described in Embodiment 1, as an emission center substance. Shown below are molecular structures of organic compounds used in this example.

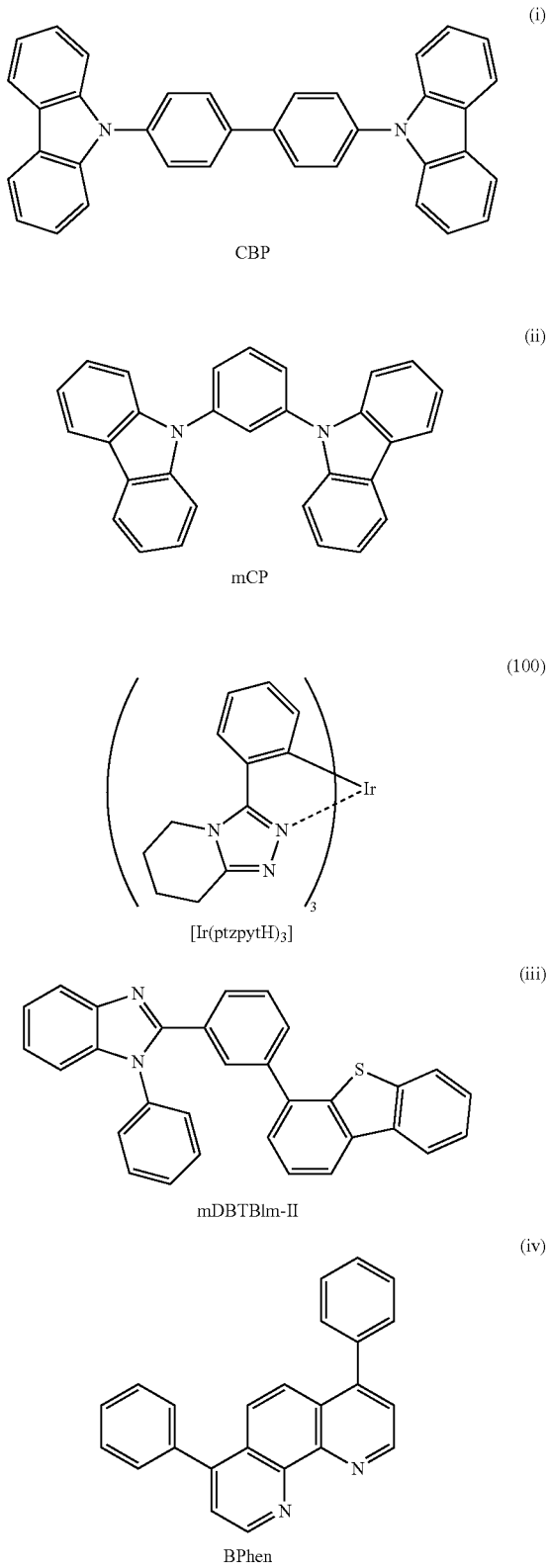

《Fabrication of Light-emitting Element》

First, a glass substrate, over which a film of indium tin oxide containing silicon (ITSO) was formed to a thickness of 110 nm as the first electrode 101, was prepared. A surface of the ITSO was covered with a polyimide film so that an area of 2 mm×2 mm of the surface was exposed. The electrode area was 2 mm×2 mm. As pretreatment for forming the light-emitting element over the substrate, the surface of the substrate was washed with water and baked at 200° C. for 1 hour, and then a UV ozone treatment was performed for 370 seconds. Then, the substrate was transferred into a vacuum evaporation apparatus where the pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate was fixed to a holder provided in the vacuum evaporation apparatus such that the surface of the substrate over which the first electrode 101 was formed faced downward.

After the pressure in the vacuum evaporation apparatus was reduced to $10^{-4}$ Pa, 4,4'-di(N-carbazolyl)biphenyl (abbreviation: CBP), which is represented by Structural Formula (I) above, and molybdenum(VI) oxide were co-evaporated so that the weight ratio of CBP to molybdenum oxide was 2:1; thus, the hole-injection layer 111 was formed. The thickness thereof was set to 50 nm. Note that the co-evaporation is an evaporation method in which a plurality of different substances is concurrently vaporized from the respective different evaporation sources.

Next, 1,3-bis(N-carbazolyl)benzene (abbreviation: mCP) which is represented by Structural Formula (II) above was deposited by evaporation to a thickness of 20 nm, so that the hole-transport layer 112 was formed.

Further, the light-emitting layer 113 was formed over the hole-transport layer 112 by forming a stacked layer in such a way that mCP and tris(3-phenyl-5,6,7,8-tetrahydro-4H-1,2,4-triazolo[4,3-a]pyridinato)iridium(III) (abbreviation: [Ir(ptzpytH)$_3$]) represented by Structural Formula (100) above, which is one of the organometallic complexes in Embodiment 1, were deposited by evaporation to a thickness of 30 nm so that the weight ratio of mCP to [Ir(ptzpytH)$_3$] was 1:0.08, and thereover, 2-[3-(dibenzothiophen-4-yl)phenyl]-1-phenyl-1H-benzimidazole (abbreviation: mDBTBIm-II) represented by Structural Formula (iii) above and [Ir(ptzpytH)$_3$] were deposited by evaporation to a thickness of 10 nm so that the weight ratio of mDBTBIm-II to [Ir(ptzpytH)$_3$] was 1:0.08.

Next, bathophenanthroline (abbreviation: BPhen) represented by Structural Formula (Iv) above was deposited by evaporation to a thickness of 15 nm, so that the electron-transport layer 114 was formed.

Further, lithium fluoride was deposited by evaporation to a thickness of 1 nm over the electron-transport layer 114, so that the electron-injection layer 115 was formed. Lastly, an aluminum film was formed to a thickness of 200 nm as the second electrode 103 functioning as a cathode. Thus, the light-emitting element was completed. Note that in the above evaporation processes, evaporation was all performed by a resistance heating method.

The element structure of the completed light-emitting element is shown below.

TABLE 1

| Functional Layer | Hole-injection Layer | Hole-transport Layer | Light-emitting Layer | | Electron-transport Layer | Electron-injection Layer |
|---|---|---|---|---|---|---|
| Thickness | 50 nm | 20 nm | 30 nm | 10 nm | 15 nm | 1 nm |
| Structure | CBP:MoOx (4:2) | mCP | mCP:Ir(ptzpytH)$_3$ (1:0.08) | mDBTBIm-II:Ir(ptzpytH)$_3$ (1:0.08) | BPhen | LiF |

《Operation Characteristics of Light-emitting Element》

The light-emitting element thus obtained was sealed in a glove box under a nitrogen atmosphere without being exposed to the air. Then, the operation characteristics of this light-emitting element were measured. Note that the measurements were carried out at room temperature (in an atmosphere kept at 25° C.).

Figure 11:
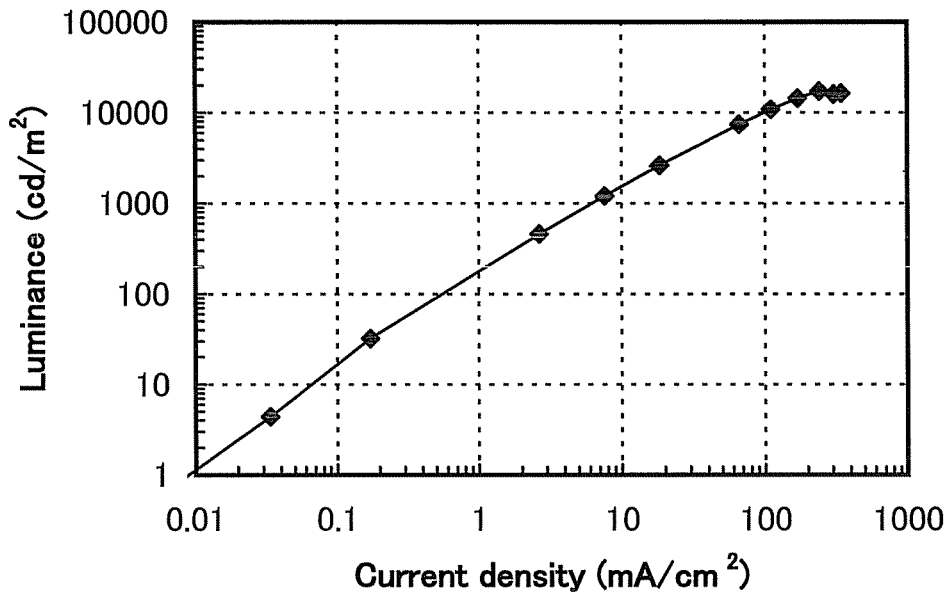
FIG. 11 shows current density-luminance characteristics of a light-emitting element fabricated in Example 1.
Figure 12:
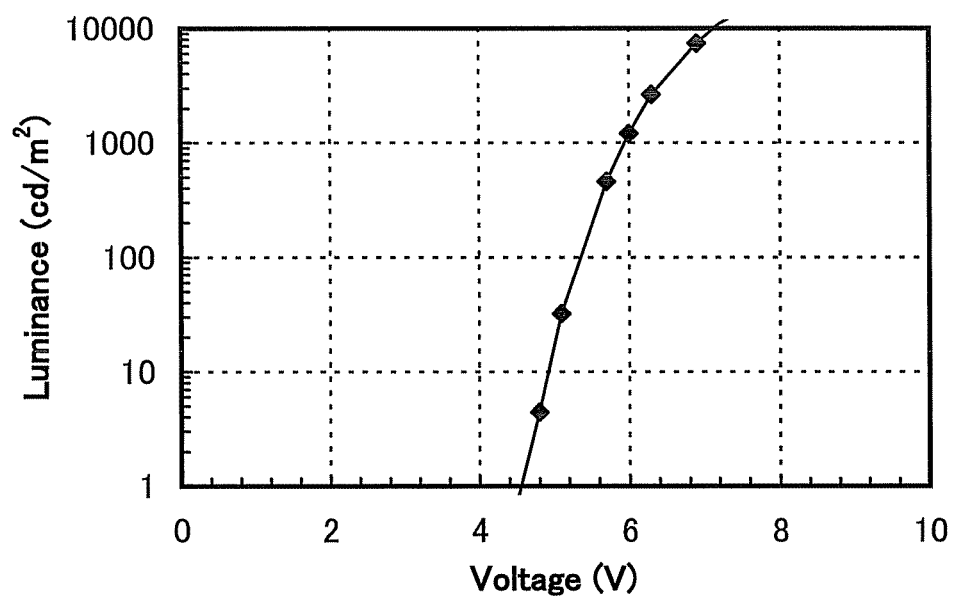
FIG. 12 shows voltage-luminance characteristics of a light-emitting element fabricated in Example 1.
Figure 13:
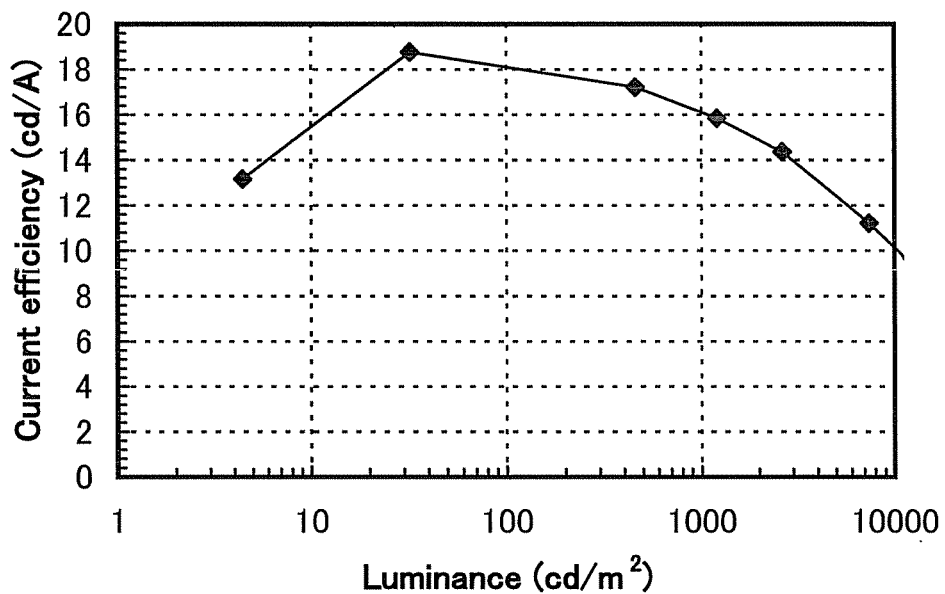
FIG. 13 shows luminance-current efficiency characteristics of a light-emitting element fabricated in Example 1.
Figure 14:
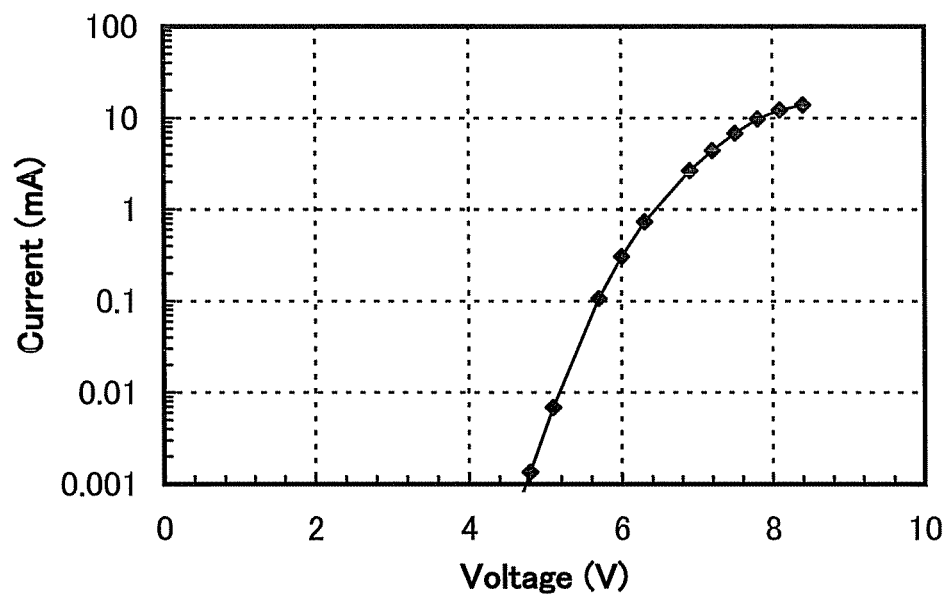
FIG. 14 shows voltage-current characteristics of a light-emitting element fabricated in Example 1.

FIG. 11 shows current density-luminance characteristics of the light-emitting element, FIG. 12 shows its voltage-luminance characteristics, FIG. 13 shows its luminance-current efficiency characteristics, and FIG. 14 shows its voltage-current characteristics. In FIG. 11, the vertical axis represents luminance (cd/m$^2$) and the horizontal axis represents current density (mA/cm$^2$). In FIG. 12, the vertical axis represents luminance (cd/m$^2$) and the horizontal axis represents voltage (V). In FIG. 13, the vertical axis represents current efficiency (cd/A) and the horizontal axis represents luminance (cd/m$^2$). In FIG. 14, the vertical axis represents current (mA) and the horizontal axis represents voltage (V).

FIG. 13 shows the favorable luminance-current efficiency characteristics of the light-emitting element of this example. Thus, the element was found to have high emission efficiency.

Figure 15:
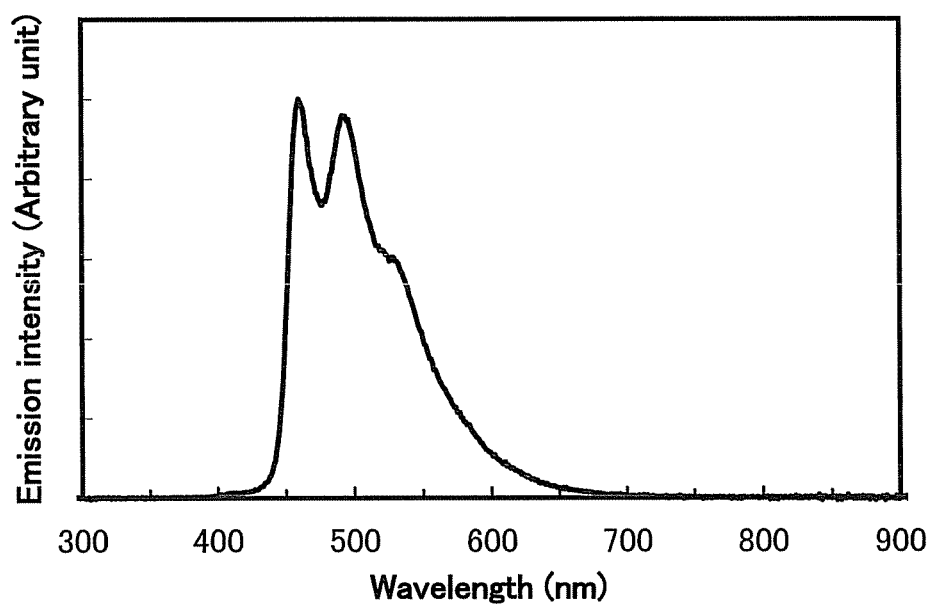
FIG. 15 shows an emission spectrum of a light-emitting element fabricated in Example 1.

FIG. 15 shows an emission spectrum when a current of 0.1 mA was made to flow in the fabricated light-emitting element. In FIG. 15, the vertical axis represents emission intensity (arbitrary unit), and the horizontal axis represents wavelength (nm). The emission intensity is shown as a value relative to the greatest emission intensity assumed to be 1. FIG. 15 shows that the light-emitting element of this example emits blue light with a maximum emission wavelength at around 460 nm.

Note that [Ir(ptzpytH)$_3$], the emission center substance of the light-emitting element of this example, is an organometallic complex capable of emitting blue phosphorescence and being manufactured inexpensively, and therefore the light-emitting element of this example can efficiently emit light in the wavelength region of blue and can be fabricated inexpensively.

This application is based on Japanese Patent Application serial no. 2011-144337 filed with Japan Patent Office on Jun. 29, 2011, the entire contents of which are hereby incorporated by reference.

What is claimed is:

1. An organometallic complex represented by General Formula (G2),

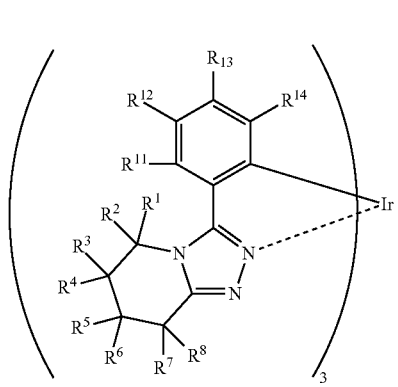

(G2)

wherein $R^1$ to $R^8$ separately represent hydrogen or an alkyl group having 1 to 4 carbon atoms, and wherein $R^{11}$ to $R^{14}$ separately represent any one of hydrogen, an alkyl group having 1 to 4 carbon atoms, an alkoxy group having 1 to 4 carbon atoms, an alkylthio group having 1 to 4 carbon atoms, a haloalkyl group having 1 to 4 carbon atoms, a halogen atom, and a phenyl group.

2. The organometallic complex according to claim 1, wherein the organometallic complex is represented by General Formula (G3)

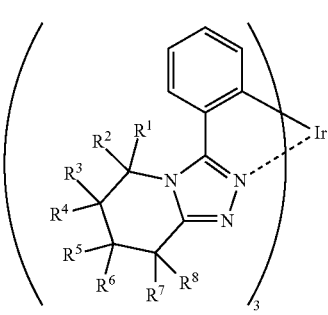

(G3)

wherein $R^1$ $R^8$ separately represent hydrogen or an alkyl group having 1 to 4 carbon atoms.

3. The organometallic complex according to claim 1, wherein the organometallic complex is represented by Structural Formula (100)

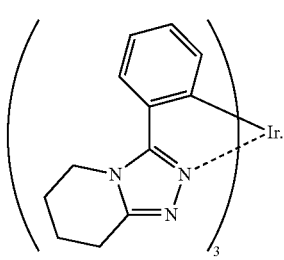

(100)

4. A light-emitting element comprising an organometallic complex between a pair of electrodes, wherein the organometallic complex is represented by General Formula (G2),

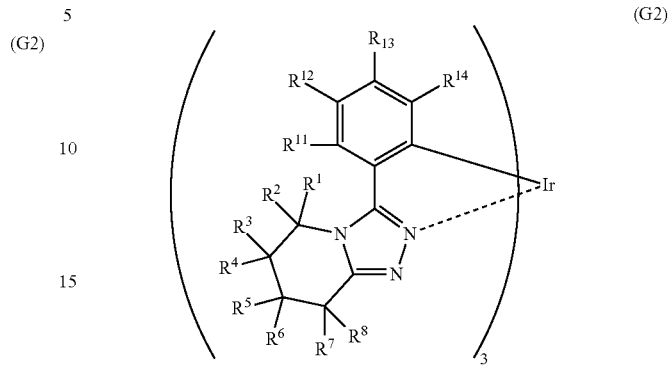

(G2)

wherein $R^1$ to $R^8$ separately hydrogen or an alkyl group having 1 to 4 carbon atoms, wherein $R^{11}$ to $R^{14}$ separately represent any one of hydrogen, an alkyl group having 1 to 4 carbon atoms, an alkoxy group having 1 to 4 carbon atoms, an alkylthio group having 1 to 4 carbon atoms, a haloalkyl group having 1 to 4 carbon atoms, a halogen atom, and a phenyl group.

5. The light-emitting element according to claim 4, wherein the organometallic complex is represented by General Formula (G3)

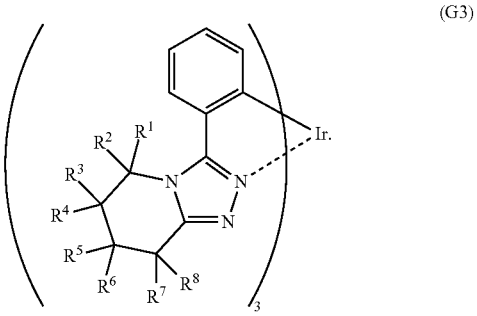

(G3)

6. The light-emitting element according to claim 4, wherein the organometallic complex is represented by Structural Formula (100)

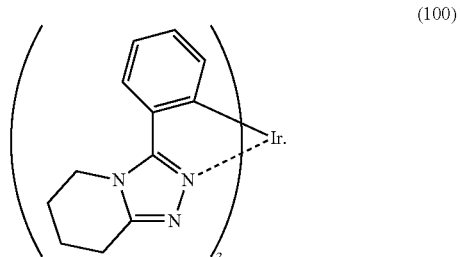

(100)

7. A display device comprising the light-emitting element according to claim 4.

8. A lighting device comprising the light-emitting element according to claim 4.

9. An organometallic complex comprising:
a metal; and
a 5-aryl-4H-1,2,4-triazole derivative,
wherein the metal is a Group 9 element or a Group 10 element,
wherein nitrogen at the 1-position of the 5-aryl-4H- 1,2,4-triazole derivative is coordinated to the metal,
wherein the 5-aryl-4H-1,2,4-triazole derivative is a 3-aryl-5,6,7,8-tetrahydro-4H-[1,2,4]triazolo[4,3-a]pyridine derivative, and
wherein the aryl group is a substituted or unsubstituted naphthylene group.

10. The organometallic complex according to claim 9,
wherein the organometallic complex is represented by General Formula (G1),

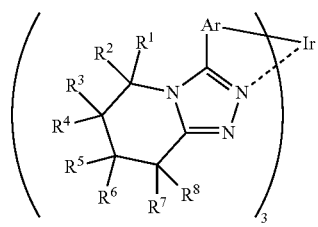

(G1)

wherein Ar represents the substituted or unsubstituted naphthylene group, and wherein $R^1$ to $R^8$ separately represent hydrogen or an alkyl group having 1 to 4 carbon atoms.

11. A light-emitting element comprising an organometallic complex between a pair of electrodes, the organometallic complex being represented by General Formula (G1),

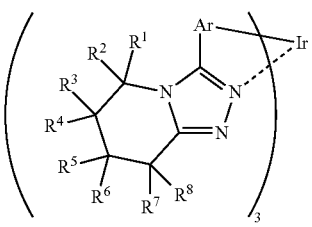

(G1)

wherein Ar represents a substituted or unsubstituted naphthylene group, wherein $R^1$ to $R^8$ separately represent hydrogen or an alkyl group having 1 to 4 carbon atoms.

* * * * *

UNITED STATES PATENT AND TRADEMARK OFFICE
CERTIFICATE OF CORRECTION

PATENT NO. : 9,273,079 B2  
APPLICATION NO. : 13/534497  
DATED : March 1, 2016  
INVENTOR(S) : Hideko Inoue et al.

It is certified that error appears in the above-identified patent and that said Letters Patent is hereby corrected as shown below:

In the Specification:

Column 2, Line 31; Change "fowls" to --forms--.

Column 2, Line 52; Change "is 3-aryl-5," to --is a 3-aryl-5,--.

Column 3, Line 57; Change "(Gl); (G2)," to --(Gl), (G2),--.

Column 7, Line 3; Change "au alkoxy" to --an alkoxy--.

Column 7, Line 29; Change "four" to --form--.

Column 17, Line 36; Change "those; pentacene," to --those, pentacene,--.

Column 20, Line 9; Change "p-type Furthermore," to --p-type TFT. Furthermore,--.

Column 27, Line 6; Change "410E" to --410G,--.

Column 29, Line 28; Change "foamed" to --formed--.

Column 32, Line 59; Change "hindered, by" to --hindered by--.

Column 37, Line 36; Change "(I) above," to --(i) above,--.

Column 37, Line 45; Change "Formula (II)" to --Formula (ii)--.

Column 37, Line 63; Change "Formula (Iv)" to --Formula (iv)--.

In the Claims:

Column 39, Line 26, Claim 1; Change "4carbon" to --4 carbon--.

Column 40, Line 20, Claim 4; Change "separately hydrogen" to --separately represent hydrogen--.

Signed and Sealed this  
Nineteenth Day of July, 2016

Michelle K. Lee  
*Director of the United States Patent and Trademark Office*

CERTIFICATE OF CORRECTION (continued)
U.S. Pat. No. 9,273,079 B2

Column 41, Lines 10 to 11, Claim 9; Change "derivative, and" to

--derivative, and wherein an aryl group at the 5-position of the 5-aryl-4H-1,2,4-triazole derivative is bonded to the metal,--.